(12) United States Patent
Kirk et al.

(10) Patent No.: US 7,419,823 B2
(45) Date of Patent: Sep. 2, 2008

(54) DEVICE AND METHOD FOR MONITORING LEUKOCYTE MIGRATION

(75) Inventors: Gregory L. Kirk, Winchester, MA (US); Emanuele Ostuni, Watertown, MA (US); Enoch Kim, Boston, MA (US); Olivier Schueller, Arlington, MA (US); Paul Sweetnam, Marblehead, MA (US)

(73) Assignee: Surface Logix, Inc., Brighton, MA (US)

( * ) Notice: Subject to any disclaimer, the term of this patent is extended or adjusted under 35 U.S.C. 154(b) by 694 days.

(21) Appl. No.: 10/688,904

(22) Filed: Oct. 21, 2003

(65) Prior Publication Data

US 2004/0142408 A1  Jul. 22, 2004

Related U.S. Application Data

(63) Continuation-in-part of application No. 10/241,445, filed on Sep. 12, 2002, which is a continuation-in-part of application No. 10/097,329, filed on Mar. 15, 2002, and a continuation-in-part of application No. 10/097,351, filed on Mar. 15, 2002, now Pat. No. 6,921,660, and a continuation-in-part of application No. 10/097,306, filed on Mar. 15, 2002, and a continuation-in-part of application No. 10/097,304, filed on Mar. 15, 2002, now Pat. No. 6,818,403, and a continuation-in-part of application No. 10/097,322, filed on Mar. 15, 2002, now Pat. No. 6,811,968, and a continuation-in-part of application No. 10/097,302, filed on Mar. 15, 2002, and a continuation-in-part of application No. 09/709,776, filed on Nov. 8, 2000, now Pat. No. 6,699,665, and a continuation-in-part of application No. 10/206,112, filed on Jul. 29, 2002, now Pat. No. 6,893,851.

(60) Provisional application No. 60/419,980, filed on Oct. 22, 2002, provisional application No. 60/419,976, filed on Oct. 22, 2002.

(51) Int. Cl.
- C12M 1/36 (2006.01)
- C12M 1/38 (2006.01)
- C12M 3/00 (2006.01)
- C12M 1/34 (2006.01)
- C12M 1/22 (2006.01)

(52) U.S. Cl. .............. 435/288.5; 435/288.4; 435/288.3; 435/287.8; 435/305.3; 435/305.1; 435/278.9

(58) Field of Classification Search .............. 435/288.5, 435/288.4, 288.3, 287.8, 305.3, 305.1, 287.9
See application file for complete search history.

(56) References Cited

U.S. PATENT DOCUMENTS 5,302,515 A  4/1994  Goodwin, Jr.

(Continued)

FOREIGN PATENT DOCUMENTS

WO   WO 00/73799 A1   12/2000

OTHER PUBLICATIONS

Michael B. Lawrence et al., "Leukoctes Roll on a Selectin at Physiologic Flow Rates: Distinction from and Prerequisite for Adhesion through Integrins", Cell (1991) 65:859-873.

(Continued)

*Primary Examiner*—Gladys Corcoran
*Assistant Examiner*—Nathan A. Bowers
(74) *Attorney, Agent, or Firm*—Kenyon & Kenyon LLP

(57) ABSTRACT

A device for monitoring leukocyte migration is provided. The invention also provides a method of using the device to monitor leukocyte migration in the presence of physiological shear flow and therefore simulate physiological conditions of a blood vessel in vivo. The invention further provides a method of using the device to high-throughput screen a plurality of test agents. The present invention further provides a flexible assay system and numerous assays that can be used to test biological interactions and systems. Laminar flow gradients are employed that mimic gradient situations present in vivo.

11 Claims, 13 Drawing Sheets

U.S. PATENT DOCUMENTS

| | | | |
|---|---|---|---|
| 5,422,270 | A | 6/1995 | Caspi |
| 5,460,945 | A | 10/1995 | Springer et al. |
| 6,238,874 | B1* | 5/2001 | Jarnagin et al. ............ 435/7.21 |
| 6,632,619 | B1 | 10/2003 | Harrison et al. |
| 6,705,357 | B2* | 3/2004 | Jeon et al. ....................... 141/9 |
| 2002/0048768 | A1* | 4/2002 | Nikiforov ....................... 435/6 |
| 2002/0168757 | A1 | 11/2002 | Kirk et al. |
| 2006/0003310 | A1* | 1/2006 | Klauke et al. ................... 435/4 |

OTHER PUBLICATIONS

Peter Marschel et al., "*Control of Fluid Shear Response in Circulating Leukocytes by Integrins*", Annals of Biomedical Engineering (2002) 30:333-343.

Monica T. Hinds et al., "*Local hemodynamics affect monocytic cell adhesion to a three-dimensional flow model coated with E-selectin*", Journal of Biomechanics (2001) 34:95-103.

Jian Tan et al., "*Micron-Scale Positioning of Features Influences the Rate of Polymorphonuclear Leukocyte Migration*", Biophysical Journal (2001) 81:2569-2579.

Pierre Thiébaud et al., "*PDMS device for patterned application of microfluids to neuronal cells arranged by microcontact printing*", Biosensors & Bioelectronics (2002) 17:87-93.

International Search Report, International Application No. PCT/US03/12764, dated Aug. 8, 2003 (3 pages).

Noo Li Jeon, et al., Neutrophil chemotaxis in linear and complex gradients of interleukin-8 formed in a microfabricated device, Nature Biotechnology, Jul. 2002, pp. 826-830, vol. 20, published on-line, doi:10.1038/nbt712.

Vereycken-Holler et al., "Radiation Effects on Circulating and Endothelial Cell Interactions Studied by Quantitative Real-Time Videomicrospy," *Int. J. Radiation Biol.*, Sep. 2002, vol. 78, No. 10, pp. 923-930, see pp. 927-928, Discussion.

Tempelman et al., "Motion of Model Leucocytes Near a Wall in Simple Shear Flow," *Biotecnol. Prog.*, 1994, vol. 10, pp. 97-108.

International Search Report, International Application No. PCT/US03/33177, dated May 20, 2004 (3 pages).

* cited by examiner

DEVICE AND METHOD FOR MONITORING LEUKOCYTE MIGRATION

CROSS-REFERENCE TO RELATED APPLICATIONS

The present application is a continuation-in-part of U.S. application Ser. No. 10/241,445 (filed Sep. 12, 2002), which is a continuation-in-part of U.S. patent application Ser. No. 10/097,329 (filed Mar. 15, 2002), U.S. patent application Ser. No. 10/097,351 (filed Mar. 15, 2002 now U.S. Pat. No. 6,921,660), U.S. patent application Ser. No. 10/097,306 (filed Mar. 15, 2002), U.S. patent application Ser. No. 10/097,304 (filed Mar. 15, 2002 now U.S. Pat. No. 6,818,403), U.S. patent application Ser. No. 10/097,322 (filed Mar. 15, 2002 now U.S. Pat. No. 6,811,968), U.S. patent application Ser. No. 10/097,302 (filed Mar. 15, 2002), U.S. patent application Ser. No. 09/709,776 (filed Nov. 8, 2000 now U.S. Pat. No. 6,699,665), and U.S. patent application Ser. No. 10/206,112 (filed Jul. 29, 2002 now U.S. Pat. No. 6,893,851). The present application also claims the benefit of U.S. Provisional Applications Nos. 60/419,980 and 60/419,976 filed on Oct. 22, 2002, the contents of which are incorporated by reference herein.

FIELD OF INVENTION

The present invention relates to devices and methods for monitoring the interaction of a cell or group of cells with a substratum. In particular, the present invention relates to devices and methods for monitoring leukocyte migration. The present invention also relates generally to biological assays performed in gradients formed in microfluidic systems.

BACKGROUND

The inflammatory response is an attempt by the body to restore and maintain homeostasis after infection or injury, and is an integral part of body defense. Most of the body defense elements are located in the blood and inflammation is the means by which these elements leave the blood and enter the tissue around the injured or infected site. The primary objective of inflammation is to localize and eradicate the source of injury or infection and repair tissue surrounding the site of injury or infection.

As a consequence of the initial innate immune response to infection, phagocytes such as mast cells in the damaged tissue release a variety of cytokines and inflammatory mediators, such as histamines, leukotrienes, bradykinins, and prostaglandins. These inflammatory mediators reversibly open the junctional zones between the thin delicate cells of the inner surface of the blood vessels, known as the endothelium, that surround the damaged tissue. The inflammatory mediators also cause increased blood vessel permeability and decreased blood flow velocity. Another result of these changes in the blood vessels is that leukocytes, which normally travel in the center of the blood vessel, move out to the periphery of the inner surface of the blood vessel to interact with the endothelium. The cytokines and inflammatory mediators released by the phagocytes also induce the expression of adhesion molecules on the surface of the endothelium, resulting in an "activated" endothelium.

The first contact of leukocytes with the activated endothelium is known as "capture" and is thought to involve the adhesion molecules P-selectin and L-selectin, which are upregulated on endothelium after exposure to inflammatory mediators. P-selectin and L-selectin belong to a family of adhesion molecules called selectins. Selectins are a group of monomeric, integral membrane glycoproteins expressed on the surface of activated endothelium and leukocytes. Selectins contain an N-terminal extracellular domain with structural homology to calcium-dependent lectins, followed by a domain homologous to epidermal growth factor, and nine consensus repeats (CR) similar to sequences found in complement regulatory proteins. There are three primary selectins thought to be involved in the inflammatory response: P-selectin; E-selectin; and L-selectin. P-selectin, also known as CD62P, GMP-140, and PADGEM, the largest selectin, is expressed on activated endothelium; E-selectin, also known as ELAM-1, is expressed on endothelium with chemically or cytokine-induced inflammation; L-selectin, also known as LECAM-1, LAM-1, Mel-14 antigen, $gp90^{mel}$, and Leu8/TQ-1 antigen, is the smallest selectin and is found on most leukocytes. All three selectins are thought to bind to selectin binding ligands, at least in part through a carbohydrate component.

During capture, P-selectin is thought to bind to its main leukocyte ligand P-selectin glycoprotein ligand-1 (PSGL-1). Other ligands of P-selectin include CD24 and yet uncharacterized ligands. The structure of functional PSGL-1 includes a sialyl-Lewis$^x$ component. In addition, during capture L-selectin is thought to bind to its ligand on endothelial cells. L-selectin interacts with three known counter receptors or ligands, MAdCAM-1, GlyCAM-1, and CD34, although the precise ligand or counter receptor involved in capture is unknown.

Once leukocytes are captured, they may transiently adhere to the endothelium and begin to "roll" along the endothelium. The term "rolling" refers to the literal rolling of leukocytes along the activated endothelium in the presence of fluid drag forces arising from the relative movement between the endothelium and the leukocytes. Rolling is thought to involve P-selectin, L-selectin, and E-selectin. Bonds between P-selectin and PSGL-1 are thought to primarily mediate the "rolling" of leukocytes across the endothelium.

Proinflammatory cytokines such as interleukin-1 (IL-1), and tumor necrosis factor-α (TNF-α) produced by cells at the injured or infected site stimulate the endothelium to produce chemokines such as interleukin-8 (IL-8) and integrin binding ligands such as intercellular adhesion molecules (ICAMs) and vascular cell adhesion molecules (VCAMs) on the surface of the endothelial cells opposite the basal lamina. The chemokines are held on the surface of the endothelial cells opposite the basal lamina where the chemokines interact with chemokine receptors on the surface of the rolling leukocytes. This interaction, in turn, triggers the activation of molecules called integrins on the surface of the leukocytes. Integrins are a family of heterodimeric transmembrane glycoproteins that attach cells to extracellular matrix proteins of the basement membrane or to ligands on other cells. Integrins are composed of large α and small β subunits. Mammalian integrins form several subfamilies sharing common β subunits that associate with different α subunits. $\beth_2$ integrins (the "CD-18 family") include four different heterodimers: CD11a/CD18 (Lymphocyte Function-Associated Antigen-1 (LFA-1)); CD11b/CD18 (Mac-1); CD11c/CD18 (p150,95); and CD11d/CD18. The most important member of the $\beth_1$ integrin subfamily on leukocytes is Very Late Antigen 4 (VLA-4, CD49d/CD29, $\forall_4\beth_1$). Activation of these integrins by chemokines enables the slowly rolling leukocytes to "arrest" and strongly bind to the endothelium's ICAMs, VCAMs, and other integrin binding ligands of the endothelial cells, such as collagen, fibronectin, and fibrinogen. Once bound to the endothelial cells, the leukocytes then flatten and squeeze between the endothelial cells to leave the blood vessels and enter the damaged tissue through a process termed "transmigration." Transmigration is thought to be mediated by platelets, endothelial cell adhesion molecule-1 (PECAM-1), junctional adhesion molecule (JAM), and possibly CD99, a transmembrane protein.

Despite their importance in fighting infection and injury, leukocytes themselves can promote tissue damage. During an abnormal inflammatory response, leukocytes can cause significant tissue damage by releasing toxic substances at the vascular wall or in uninjured tissue. Alternatively, leukocytes may stick to the capillary wall or clump in venules to such a degree that the endothelium becomes lined with these cells. Such a phenomenon, referred to as "pavementing," may be related to the development of arteriosclerosis and associated diseases. Such abnormal inflammatory responses have been implicated in the pathogenesis of a variety of other clinical disorders including adult respiratory distress syndrome (ARDS); ischemia-reperfusion injury following myocardial infarction, shock, stroke, or organ transplantation; acute and chronic allograft rejection; vasculitis; sepsis; rheumotoid arthritis; and inflammatory skin diseases.

Several methods and devices exist in the art to study the processes of leukocyte migration implicated in these various inflammatory diseases. For example, one method involves plating a monolayer of isolated endothelial cells on the surface of microtiter plates, activating the cells with a chemoattractant and then placing labeled leukocytes in the plate. A test agent, such as an adhesion inhibitor, may be optionally added to the plate. The number of leukocytes that remain adherent to the endothelial cell monolayer is then determined. A significant disadvantage of this method is that the leukocytes are not exposed to the endothelial cells in the presence of shear flow and thus this method does not simulate physiological conditions in vivo.

Another method involves contacting a suspension of isolated leukocytes in a suitable medium with a human vascular tissue sample mounted on a microscope slide and then incubating the tissue with a cell suspension on a rotating table. The adhered cells are fixed and counted. Because cells are fixed, such a method precludes the observation of leukocyte migration in real time. In addition, such a method requires human vascular tissue, which can be difficult and costly to obtain.

Another method known in the art to study leukocyte migration, involves a device consisting of two glass tubes called microslides, one microslide capable of being inserted into the other. The smaller microslide is inserted into the larger one to create a flow channel with a flat surface on which selected adhesion molecules are present. A suspension of leukocytes is then perfused through the flow channel over the adhesion molecule immobilized surface using a syringe pump. The rolling and adhesion of the leukocytes is then observed. Because of the size and configuration of this device, it requires considerable handling and manipulation.

Another device to study leukocyte migration during the inflammatory response is described in U.S. Pat. No. 5,460,945 to Springer et al. entitled "Device and Method for Analysis of Blood Components and Identifying Inhibitors and Promoters of the Inflammatory Response." This device consists of several different components that are bulky in size. As such, it requires extra handling and positioning, creating the risk of contaminating or damaging the endothelial monolayer. This device also requires the use of a large number of cells and consequently a large amount of reagents.

Therefore, there exists a need for an improved device to study the leukocyte migration along the endothelium that simulates the physiological conditions of a blood vessel. There also exists a need for a device that would allow for high throughput screening of test agents that potentially affect the interaction of leukocytes with the endothelium without requiring the number of leukocytes per assay as required by the devices currently known in the art. The present invention meets these needs.

SUMMARY OF THE INVENTION

The present invention provides a system for monitoring leukocyte migration comprising a device including a housing defining a plurality of chambers therein. Each of the plurality of chambers includes a first well region including at least one first well, a second well region including at least one second well, and a channel region including at least one channel connecting the first well region and the second well region with one another. The system further includes a first fluid stream having a first concentration of a first substance and a second fluid stream having a second concentration of a second substance, wherein the first and second concentrations are different from one another and the first and second fluid streams are in fluid communication with at least one of the plurality of chambers.

The present invention also provides a method of monitoring leukocyte migration comprising disposing endothelial cells on a surface, passing a fluid along the surface under conditions of substantially laminar flow wherein the fluid comprises a concentration gradient of at least one substance. The concentration gradient is substantially perpendicular to the direction of flow. The method further includes exposing a sample comprising leukocytes to the surface, and observing the interaction between the leukocytes and the endothelial cells.

The present invention moreover provides a method of monitoring leukocyte migration comprising providing a device including a housing defining a plurality of chambers therein. Each of the plurality of chambers includes a first well region including at least one first well, a second well region including at least one second well, and a channel region including at least one channel connecting the first well region and the second well region with one another. The method further comprises disposing at least one leukocyte migration mediator, or endothelial cells in the at least one channel, delivering a sample comprising leukocytes to the at least one channel by laminar flow, and observing the interaction between the leukocytes and the at least one leukocyte migration mediator or the interaction between the leukocytes and the endothelial cells.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION

Definitions

Figure 1:
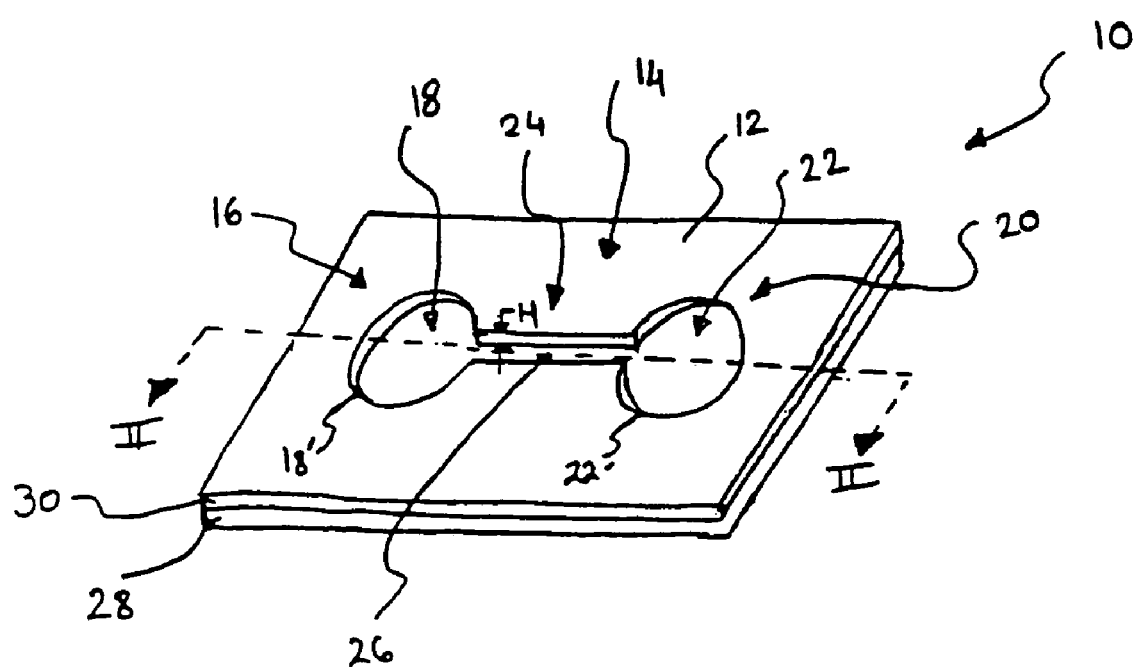
FIG. 1 is a perspective view of an embodiment of a device adapted to be used in a method for monitoring leukocyte migration according to the present invention.

It is understood that the terminology and definitions used herein are for the purpose of describing particular embodiments only and are not intended to be limiting.

The term "leukocytes" as used herein refers to granulocytes including neutrophils, eosinophils, basophils, monocytes, and lymphocytes including B cells and T cells and unless otherwise specified, platelets. The term "leukocytes" includes leukocytes obtained from both normal blood samples and pathological blood samples.

The term "leukocyte migration cascade" refers to the cascade of sequential events involving a leukocyte's migration along the endothelium lining a blood vessel. The leukocyte migration cascade includes the capture, rolling, arrest, and transmigration of a leukocyte on, along, or through the endothelium.

The term "leukocyte migration mediator" as used herein refers to any molecule that mediates the migration of leukocytes along the endothelium lining a blood vessel. The term "mediates" as used in the context of a "leukocyte migration mediator" means influencing the migration of a leukocyte by, for example, binding to the ligand or counter-receptor of the leukocyte migration mediator. In particular, the term "leukocyte migration mediator" refers to any molecule involved in the leukocyte migration cascade. As such, a leukocyte migration mediator includes a leukocyte capture mediator, a leukocyte rolling mediator, a leukocyte arrest mediator, a leukocyte transmigration mediator, or any combination thereof.

The term "capture" as used herein refers to a step in the leukocyte migration cascade characterized by the tethering or first contact of leukocyte with the endothelium of a blood vessel so that the motion of the leukocyte along the endothelium is temporarily delayed relative to the flow of fluid containing free flowing leukocytes.

The term "leukocyte capture mediator" as used herein refers to a leukocyte migration mediator that mediates the capture of a leukocyte on the endothelium of a blood vessel. Non-limiting examples of leukocyte capture mediators are P-selectin and L-selectin binding ligands.

The term "capture mediator binding partner" refers to any ligand or counter-receptor that binds a leukocyte capture mediator. Non-limiting examples of capture mediator binding partners are PSGL-1 and L-selectin.

The term "rolling" as used herein refers to a step in the leukocyte migration cascade, and is characterized by the rolling of a leukocyte along the endothelium of a blood vessel from receptor to receptor on the endothelium further characterized by leukocytes forming and breaking adhesive bonds with endothelial ligands or counter-receptors.

The term "leukocyte rolling mediator" as used herein refers to any leukocyte migration mediator that mediates the rolling of a leukocyte along the endothelium of a blood vessel. Non-limiting examples of leukocyte rolling mediators are P-selectin, E-selectin, and L-selectin binding ligands.

The term "rolling mediator binding partner" as used herein refers to any ligand or counter-receptor that binds to a leukocyte rolling mediator. Non-limiting examples of rolling mediator binding partners are PSGL-1, E-selectin binding ligand, and L-selectin.

The term "arrest" as used herein refers to a step in the leukocyte migration cascade characterized by the adherence of leukocytes to the endothelium of a blood vessel.

The term "leukocyte arrest mediator" as used herein refers to any leukocyte migration mediator that mediates the arrest of a leukocyte on the endothelium of a blood vessel. Non-limiting examples of arrest mediators are integrin binding ligands, such as ICAM-1, ICAM-2, and VCAM-1 that bind integrins expressed on the surface of leukocytes.

The term "arrest mediator binding partner" as used herein refers to any ligand or counter-receptor that binds to a leukocyte arrest mediator. Non-limiting examples of arrest mediator binding partners are integrins including LFA-1, Mac-1, p150,95, VLA-4, and VLA-5.

The term "transmigration" as used herein refers to a step in the leukocyte migration cascade characterized by the exit of leukocytes from a blood vessel to surrounding tissue through passage between cells of the endothelium of the blood vessel.

The term "leukocyte transmigration mediator" as used herein refers to any leukocyte migration mediator that mediates the transmigration of a leukocyte through the endothelium of a blood vessel. Non-limiting examples of leukocyte transmigration mediators are PECAM-1 and JAM.

The term "transmigration binding partner" as used herein refers to any ligand or counter-receptor that binds to a leukocyte transmigration mediator.

The term "physiological shear flow" includes shear flow under normal and pathological conditions. Physiological shear flow rate under normal conditions is about 0.1 to about 20 dynes/cm$^2$.

The term "test agent" as used herein refers to any chemical molecule or compound to be tested in the present invention to determine its ability to interact with another chemical molecule or compound. For example, the test agent may be tested to determine whether it inhibits or promotes leukocyte migration by inhibiting or promoting capture, rolling, arrest, or transmigration.

The term "pitch" as used herein refers to the distance between respective vertical centerlines between adjacent wells in the test orientation of the device.

The term "well region" as used herein is meant to refer to a region that comprises one or a plurality of wells.

The term "well" as used herein is meant to indicate any cavity that is able to receive a fluid therein.

The term "channel region" as used herein refers to a region that comprises one or a plurality of channels therein, while "channel" refers to any passageway.

In the context of the present invention, "conformal contact" is meant to designate a substantially fluid-tight, form-fitting contact with a planar or non-planar surface, and "reversible conformal contact" is meant to designate a conformal contact that may be interrupted without compromising a structural integrity of the members making the conformal contact.

In the context of the present invention, the "test orientation" of the device is meant to refer to a spatial orientation of the device during the monitoring of leukocyte migration and the terms "top," "bottom," "upper" and "side" are defined relative to the test orientation of the device. In one embodiment, the test orientation of the device for use in a method of monitoring leukocyte migration contemplates the orientation of the device such that a migration path along the channel region of any cells occurs in a substantially horizontal plane. In another embodiment, the test orientation of the device for use in monitoring leukocyte migration contemplates the orientation of the device such that a migration path along the channel region of any cells occurs in a substantially vertical plane.

The present invention generally provides devices and methods for in vitro monitoring the interaction of cells with a substratum. Non-limiting examples of cell types that may be monitored by the devices and methods of the present invention include leukocytes, red blood cells, platelets, non-blood cells, and tumor cells. Non-limiting examples of types of substratum that may interact with the cells include the endothelium, immobilized ligands, physisorbed adhesion and rolling molecules and basal lamina or basal lamina mimic. In particular, the present invention provides a device and method for in vitro monitoring of leukocyte migration in the presence of shear flow in order to study the cascade of events involved in the inflammatory response in vivo. The present invention also provides a device and method for the high-throughput screening of test agents that potentially target these events. In particular, the present invention is directed to study and target the capture, rolling, arrest, and transmigration of a leukocyte on, along, or through the endothelium (such events collectively referred to as the "leukocyte migration cascade").

Figure 3:
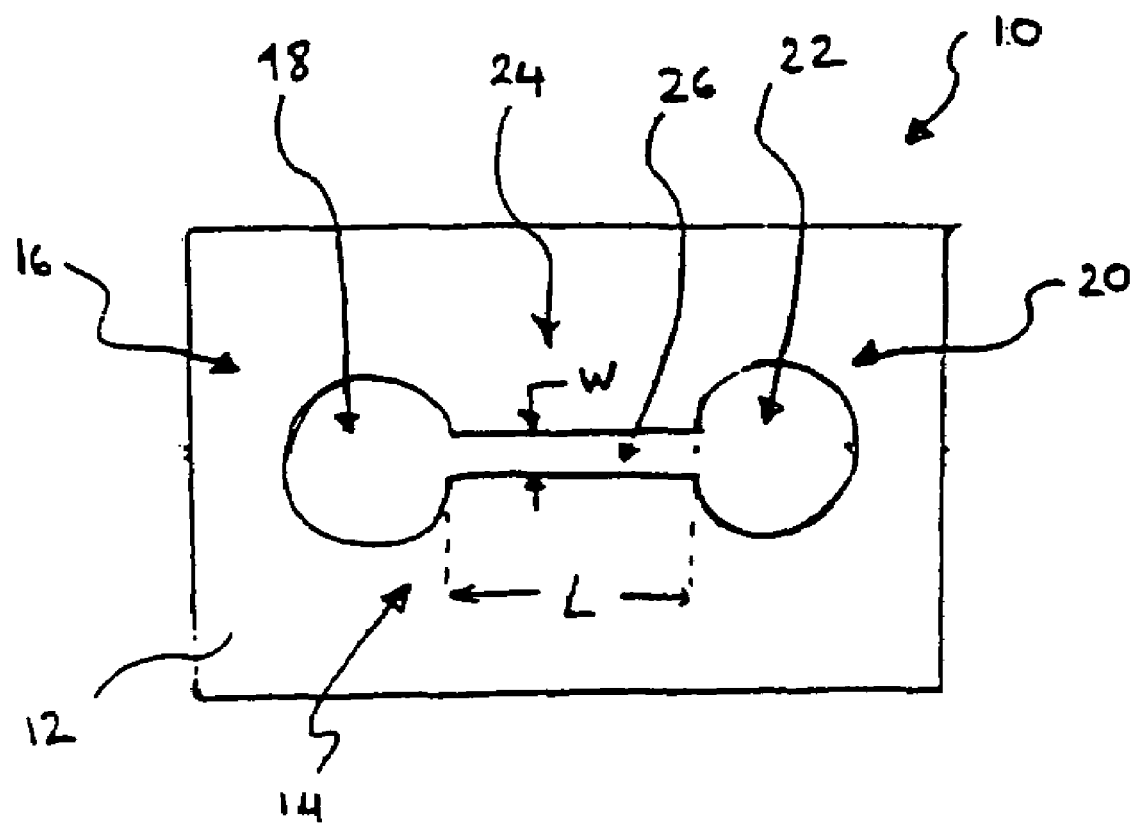
FIG. 3 is a top plan view of the device of FIG. 1.
Figure 4:
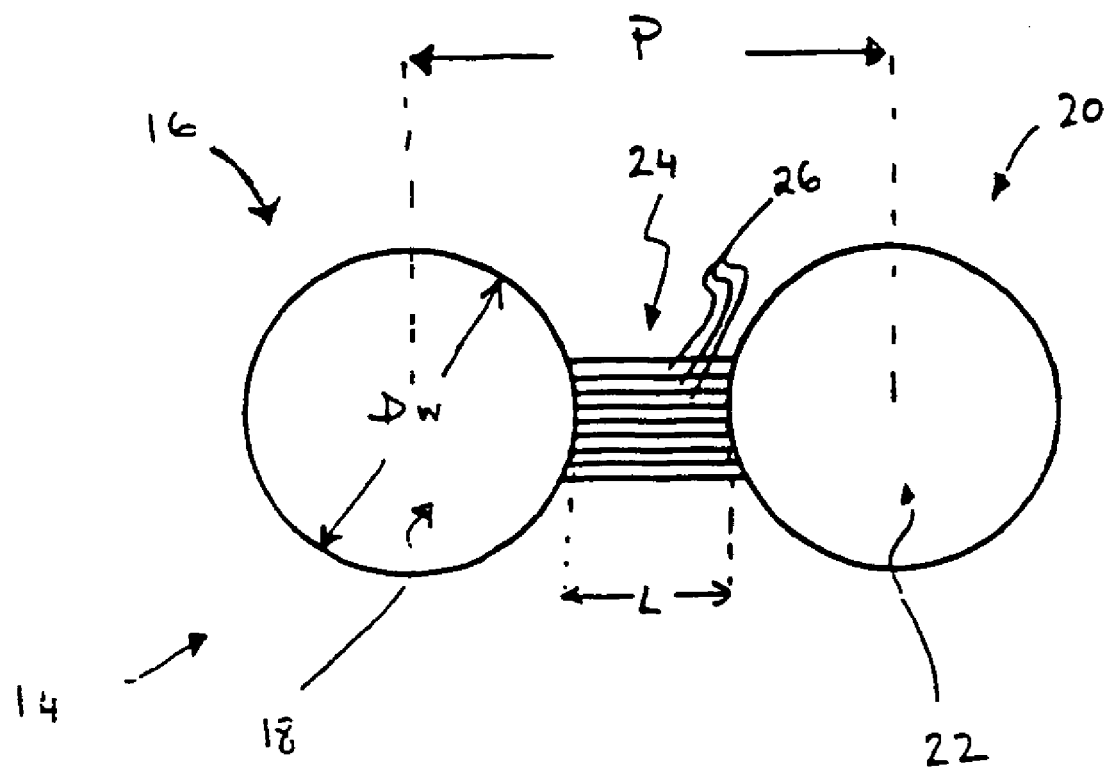
FIG. 4 is a top plan view of an alternative embodiment of a chamber defined in a housing of a device adapted to be used in a method for monitoring leukocyte migration according to the present invention.
Figure 5:
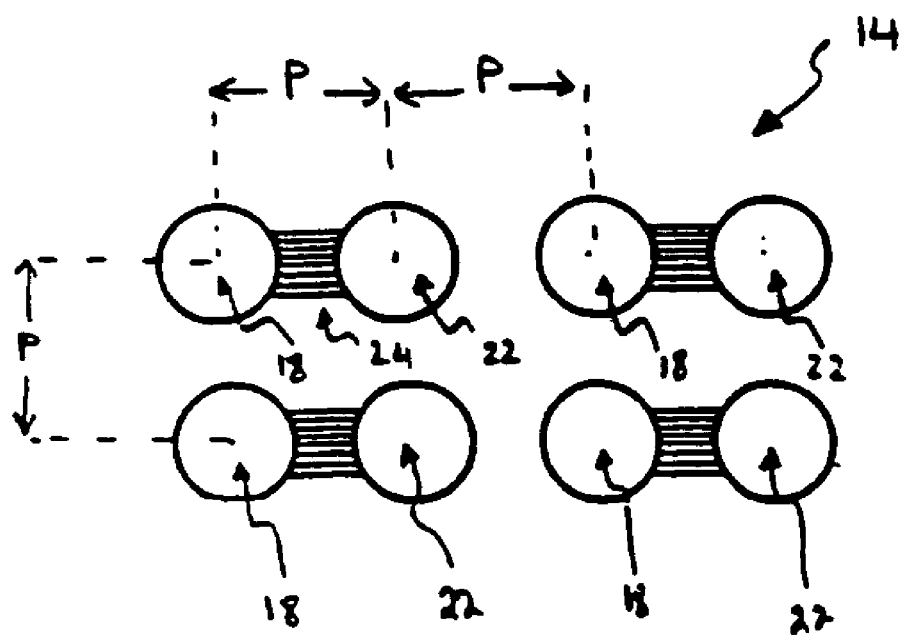
FIG. 5 is a top plan view of a plurality of chambers such as the chamber of FIG. 4 disposed in a predetermined relationship with respect to one another.
Figure 6:
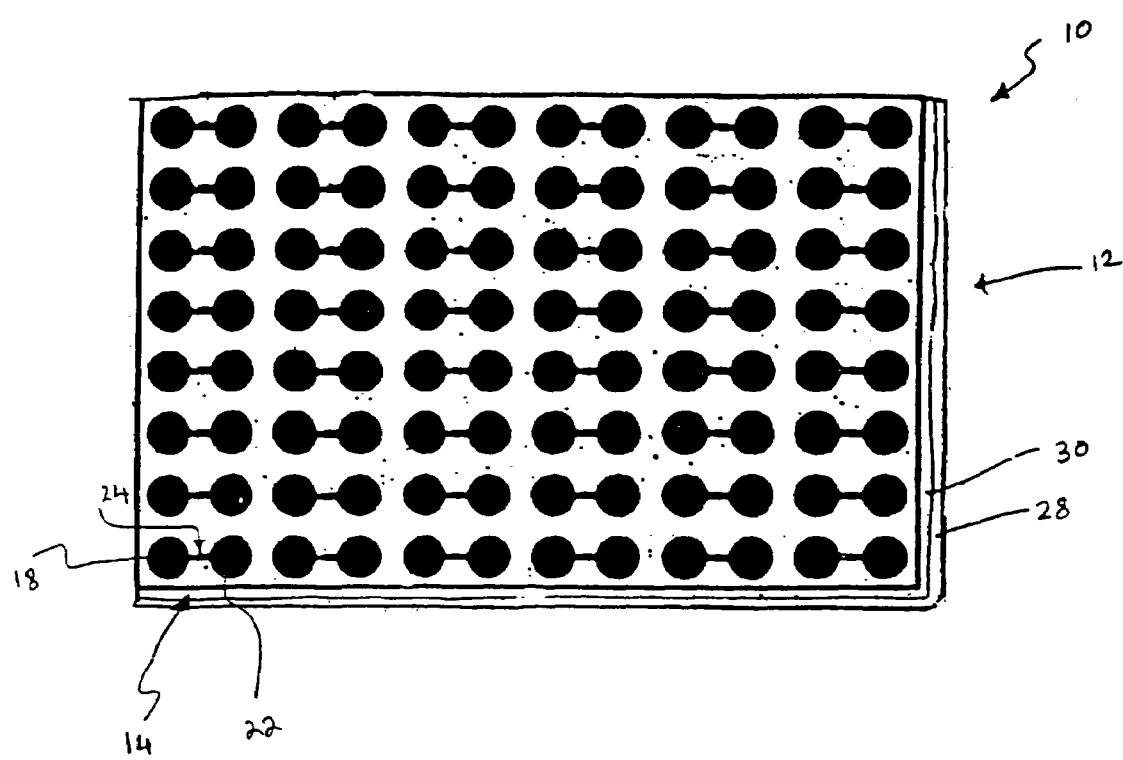
FIG. 6 is a top, perspective view of an alternative embodiment of a device adapted to be used in a method for monitoring leukocyte migration according to the present invention, where the device displays the dimensions and pitch of a standard 96-well microtiter plate.

As schematically depicted in FIGS. 1-6, device 10 generally includes a housing 12 defining a plurality of chambers 14 therein, such as, by way of example, embodiments of chamber 14 depicted in FIGS. 1-6. Each chamber 14 includes: a first well region 16 including at least one first well 18 and a second well region 20 including at least one second well 22. The chamber 14 further includes a channel region 24 including at least one channel 26 connecting the first well region 16 and the second well region 20 with one another. As illustrated in FIGS. 5 and 6, in a preferred embodiment, the first well regions 16 and the second well regions 20 of the respective ones of the plurality of chambers are disposed relative to one another to match a pitch of a standard microtiter plate. The plurality of chambers may also be disposed relative to one another to match a pitch of standard microtiter plate. Generally, first well 18 and second well 22 are adapted to receive a sample comprising leukocytes and channel 26 is adapted to receive endothelial cells or leukocyte migration mediators thereon and is configured to support physiological shear flow therealong.

In one embodiment of the present invention, channel 26 contains endothelial cells disposed therein. The endothelial cells may be activated prior to exposure to channel 26 or may have chemokines immobilized on the surface opposite the basal lamina therein upon exposure to channel 26. Various cytophilic substances may be disposed in channel 26 to assist in the attachment of endothelial cells. Cytophilic substances are generally substances that have an affinity for cells or substances that promote cell attachment to the surface and include, for example, gelatin, collagen, fibronectin, fibrin, basal lamina, including, but not limited to MATRIGEL™ or other hydrogels.

In another embodiment of the present invention, channel 26 includes a plurality of leukocyte migration mediators disposed therein. Preferably, the plurality of leukocyte migration mediators comprises at least one first leukocyte migration mediator and at least one second leukocyte migration mediator, wherein the at least one first and the at least one second leukocyte migration mediators are different from one another. The leukocyte migration mediators are disposed in channel 26 so as to form a surface concentration gradient along a longitudinal axis of chamber 14 in increasing concentration from first well 18 to second well 22.

In yet another embodiment of the present invention, channel 26 includes chemokines disposed therein to interact with chemokine receptors on the surface of rolling leukocytes.

The present invention also contemplates a method of monitoring leukocyte migration. In one embodiment where channel 26 contains endothelial cells disposed therein, a sample including leukocytes is placed in first well 18 (or second well 22), the sample is allowed to flow along channel 26, the interaction (such interaction including a lack thereof) between the leukocytes and the endothelial cells is observed, and the sample including leukocytes is collected in second well 22 (or the first well 18) as the leukocytes exit channel 26. A chemoattractant may be added to channel 26 to activate the endothelial cells before a sample containing leukocytes is added to first well 18 (or second well 22). In one embodiment, a test agent is placed in channel 26 and the interaction between the leukocytes and endothelial cells in the presence of the test agent is observed.

In one embodiment where channel 26 contains a leukocyte migration mediator disposed therein, a sample including leukocytes is placed in first well 18 (or second well 22), the sample is allowed to flow along channel 26, the interaction (such interaction including a lack thereof) between the leukocytes and the leukocyte migration mediator is observed, and the sample including leukocytes is collected in second well 22 (or the first well 18) as the leukocytes exit channel 26. In one embodiment, a test agent is placed in channel 26 and the interaction between leukocytes and the leukocyte migration mediator in the presence of the test agent is observed.

Figure 6A:
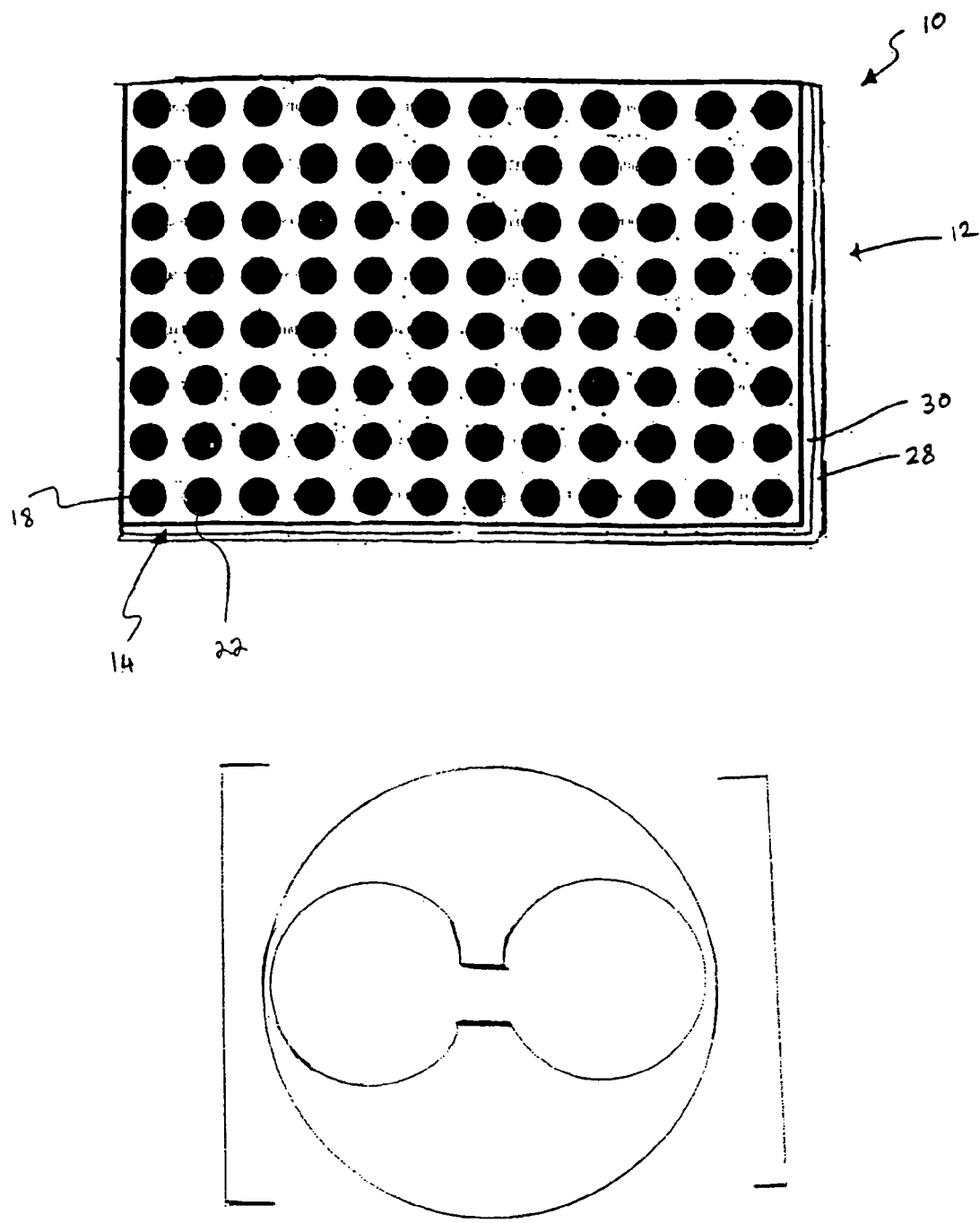
FIG. 6A is a top enlarged view of an individual well of an alternative embodiment of the device according to the present invention.

Because device 10, or elements of device 10, may match the footprint of an industry standard microtiter plate, an advantage of device 10 is that device 10 may be used to conduct multiple assays simultaneously in the same device, and to high throughput screen various test agents. In one preferred embodiment, as illustrated in FIG. 5, the first well regions 16 and the second well regions 20 of the respective ones of the plurality of chambers 14 are disposed relative to one another to match a pitch of a standard microtiter plate. Taking P to designate a pitch between respective wells 18/22, the wells may be disposed relative to one another to match a pitch of one of a 24-well microtiter plate, a 96-well microtiter plate, a 384-well microtiter plate, 768-well microtiter plate and a 1536-well microtiter plate. By way of example, in the configuration of chambers 14 as shown in FIG. 5, pitch P will be set to about 9 mm. Preferably, device 10 itself fits in the footprint of an industry standard microtiter plate. As such, device 10 preferably has the same outer dimensions and overall size of an industry standard microtiter plate. By way of example, in the configuration of device 10 as shown in FIG. 6, device 10 comprises 48 chambers designed in the format of a standard 96-well plate, such that the respective wells 18/22 are disposed relative to one another to match a pitch of a standard 96-well microtiter plate with each well fitting in the space of each well of the plate. In this embodiment, 48 experiments can be conducted. Alternatively, as seen in FIG. 6A, chambers 14 may be disposed relative to one another to match a pitch of a standard microtiter plate. In this alternative embodiment, chambers 14 are sized so that a chamber 14 fits in the area normally required for a single well of a standard microtiter plate. For example, in this embodiment, device 10, designed in the footprint of a 96-well microtiter plate configuration, has 96 chambers and therefore allows 96 experiments to be performed. By conforming to the exact dimensions and specification of standard microtiter plates, embodiments of device 10 would advantageously fit into existing infrastructures of fluid handling, storage, registration and detection. Device 10 is also conducive to high throughput screening as it allows robotic fluid handling and automated detection and data analysis. The use of robotic and automated systems also decreases the amount of time to prepare and perform the assays and analyze the results of the assays. In addition, by using automated systems, the use of device 10 decreases the occurrence of human error in preparing and performing assays and analyzing data. Moreover, because the size of the wells 18/22, or the size of an entire chamber 12, of device 10 matches the size of a well of a microtiter plate, the number of leukocytes needed to perform an individual assay range from only about 103 to about 106. This allows for the study of rare leukocyte populations, such as basophils or certain lymphocyte subsets. In addition, large amounts of test agents, such as inhibitors and promoters of leukocyte migration, need not be used in order to conduct assays monitoring the effect of these agents on leukocyte migration.

Based on the preferred configuration of device 10, the present invention also contemplates a method of screening a plurality of test agents. In this embodiment, the method of screening test agents includes providing a device comprising a housing defining a plurality of chambers. Each chamber includes: a first well region including at least one first well; a second well region including at least one second well; and a channel region including at least one channel connecting the first well region and the second well region with one another. In one embodiment, the at least one channel includes at least one leukocyte migration mediator disposed therein. In another embodiment, the at least one channel includes endothelial cells disposed therein. In both preferred embodiments, at least one of the plurality of chambers on the one hand, and the first well regions and the second well regions of respective ones of the plurality of chambers on the other hand, are disposed relative to one another to match a pitch of a standard microtiter plate. The method of screening test agents further includes providing leukocytes in each of the channels of respective ones of the plurality of chambers; placing at least one of a plurality of test agents in each of the channels of respective ones of the plurality of chambers; and observing the interaction between the leukocytes and the endothelial cells or the interaction between the leukocytes and the at least one leukocyte migration mediator in the presence of the test agents. For example, it can be determined whether the test agents have an effect on the number of leukocytes that are captured, arrested, or have transmigrated as well as whether the test agents have an effect on velocity and number of leukocytes that roll along channel 26. The test agent may include any desired biological, chemical, or electrical substance, including but not limited to, an inhibitor of leukocyte migration, a promoter of leukocyte migration, or any other therapeutic agent. Further examples of test agents include proteins, nucleic acids, peptides, polypeptides, carbohydrates, lipids, hormones, enzymes, small molecules or pharmaceutical agents. This method is particularly useful in the area of drug discovery where a plurality of test agents may be screened in a single device 10. Accordingly, it is preferable that each of the test agents is different from one another and a single test agent is placed in each channel. Of course, if it is desirable to test the effects of a combination of test agents, for example to determine if there is any synergistic effect of two or more test agents, than two or more test agents of the plurality of test agents may be placed in each channel of each of the plurality of chambers.

The device of the present invention may also be used to monitor the steps of the leukocyte migration cascade under a normal or pathological physiological shear flow condition. A normal physiological flow condition refers to the shear flow rate during a non-pathological state and is in the range of about 0.1 dynes/cm$^2$ to about 20 dynes/cm$^2$. A pathological physiological flow condition refers to the shear flow rate during the inflammatory response and is generally varied depending on the disease state. Although the physiological shear flow is preferably produced by hydrostatic pressure, or microcapillary action, the flow can be produced by any means known in the art. For example, if a sample containing leukocytes is to be introduced into channel 26 via first well 18, then physiological shear flow can be created by applying pressure through a vacuum adjacent to second well 22 or by applying pressure through a syringe pump adjacent to first well 18. The shear flow may be manipulated by altering the dimensions of the channels or modifying the degree of pressure applied through the vacuum or syringe pump. Alternatively, the leukocytes can be introduced into channel 16 in a pulsatile manner.

With respect to particular embodiments of device 10 and methods of using these embodiments, as mentioned above, channel 26 may have endothelial cells disposed therein or leukocyte migration mediators disposed therein. The endothelial cells may be disposed on any surface or surfaces of channel 26. In a preferred embodiment, the endothelial cells are on the bottom and side surfaces of channel 26. The endothelial cells may be disposed uniformly in channel 26, may be disposed in discrete patches, or may be disposed along a concentration gradient such that the concentration of endothelial cells decreases from first well 18 to second well 22. The endothelial cells may be grown on channel 26 in the presence or absence of shear flow. In one embodiment where channel 26 has endothelial cells disposed therein, several different assays may be performed to observe the interaction between leukocytes and the endothelial cells during the leukocyte migration cascade. For example, to study the process of rolling, a sample containing leukocytes is introduced into channel 26 via first well 18 or second well 22. The number of leukocytes rolling as well as the rolling velocity of the leukocytes may then be determined. Assays measuring the inhibition of rolling may also be performed by adding to channel 26, for example, inhibitors that block the interaction between leukocytes and endothelial cells. Similarly, assays measuring the enhancement of rolling may be performed by adding to channel 26, for example, promoters that promote the interaction between leukocytes and endothelial cells. A test agent could also be added to channel 26 to determine the effect of the test agent on the interaction between leukocytes and endothelial cells.

To study the process of arrest, preferably a chemoattractant is introduced into channel 26 in order to "activate" the endothelium. The chemoattractants may be any molecule suitable to stimulate the endothelium to express integrin binding ligands such as ICAMs and VCAMs. Non-limiting examples of chemoattractants include cytokines such as IL-1 and TNF-α. A sample including leukocytes is then introduced in channel 26 via first well 18 or second well 22. Preferably, the sample including leukocytes is preincubated with a chemoattractant capable of triggering the activation of arrest mediator binding partners, for example integrins, on the surface of leukocytes. The chemoattractant is any suitable substance capable of triggering integrin expression by leukocytes and includes, for example, formyl peptides, intercrines, IL-8, GRO/MGSA, NAP2, ENA-78, MCP-1/MCAF, RANTES, I-309, other peptides, platelet activating factor (PAF), lymphokines, collagen, fibrin, and histamines. The number of arrested cells may then be determined. Assays measuring the inhibition of arrest may also be performed, for example, by adding inhibitors that block the interaction between chemoattractants and chemoattractant receptors on the surface of the leukocytes or the endothelium, or that block the interaction between leukocyte arrest mediators and arrest mediator binding partners. A test agent could also be added to channel 26 to determine the interaction between the leukocytes and the endothelial cells in the presence of the test agent.

In another embodiment directed to examining the process of transmigration, a layer of endothelial cells is placed in channel 26. In a preferred embodiment to more closely simulate in vivo conditions, channel 26 may first be coated with a layer of fibronectin or any other basement membrane mimic before adding the endothelial cells to channel 26. Preferably the endothelial cells are exposed to eotaxins or chemokines, including RANTES or monocyte chemoattractant protein (MCP-3 or MCP-4) prior to introduction of the sample containing leukocytes. The sample including leukocytes is then introduced into channel 26 via first well 18 or second well 22. Preferably, the leukocytes are preincubated with a chemoattractant capable of triggering the activation of arrest mediator binding partners, for example integrins, on the surface of leukocytes. After the leukocytes are allowed to flow along channel 26, the number of cells that transmigrated through the endothelium are counted. Transmigrated cells may be characterized by appearing flattened and phase-dark under a microscope. Flattened, phase-dark cells may be confirmed as being under the endothelial cell monolayer by observing the focal plane of the leukocytes and the endothelial cells using a microscope. A cell may be considered transmigrated if, for example, greater than 50% of the cell is under the endothelial cell monolayer at the point of quantification. Transmigration may be expressed as the number of transmigrated cells divided by the total cells counted. Inhibition of transmigration may also be examined by blocking, for example, the receptor on endothelium cells that binds the chemoattractant responsible for activating the endothelium and then determining the number of cells that transmigrate across the endothelium. A test agent may also be introduced in channel 26 to determine the interaction between the leukocytes and the endothelial cells in the presence of the test agent.

In another embodiment, the endothelial cells disposed in channel 26 have been altered or modified through known techniques in molecular biology. For example, the cells may be modified to overexpress particular genes or to not express particular genes coding for the various leukocyte migration mediators responsible for the leukocyte migration cascade. Such an embodiment affords control over the expression of precise leukocyte migration mediators and allows greater manipulation of the mediator involved in the leukocyte migration cascade.

For example, the endothelial cells may be genetically modified to reduce or inhibit the expression of a gene believed to encode a protein involved in the leukocyte migration cascade to assist in the elucidation of the proteins involved in leukocyte migration cascade. Methods for genetically modifying a cell are known in the art. One such method is disclosed in U.S. Pat. No. 6,025,192 to Beach et al. and involves replication-deficient retroviral vectors, libraries comprising such vectors, retroviral particles produced by such vectors in conjunction with retroviral packaging cell lines, integrated provirus sequences derived from the retroviral particles of the invention and circularized provirus sequences which have been excised from the integrated provirus sequences of the invention.

In another non-limiting example, the endothelial cells may be transfected with a vector to genetically modify a protein expressed by the endothelial cells. For various techniques for transfecting mammalian cells, see Keown et al. (1990) Methods in Enzymology 185:527-537. For example, the endothelial cells may be modified to express a variant of the protein to be tested. For example, if it is believed that a certain protein is involved in the cascade, the gene expressing the particular protein can be modified to express a variant. Then using the device and assays of the present invention, the effect of this variant on the various parts of the cascade can be monitored.

The variant can be created using techniques known in the art by making deletions, additions or substitutions in the sequence encoding the protein. A "variant" of a polypeptide is defined as an amino acid sequence that is altered by one or more amino acids. Similar minor variations can also include amino acid deletions or insertions, or both. Guidance in determining which and how many amino acid residues may be substituted, inserted or deleted without abolishing biological or immunological activity can be found using computer programs well known in the art, for example, DNAStar software. A "deletion" is defined as a change in either amino acid or nucleotide sequence in which one or more amino acid or nucleotide residues, respectively, are absent as compared to an amino acid sequence or nucleotide sequence of a naturally occurring polypeptide. An "insertion" or "addition" is that change in an amino acid or nucleotide sequence which has resulted in the addition of one or more amino acid or nucleotide residues, respectively, as compared to an amino acid sequence or nucleotide sequence of a naturally occurring polypeptide. A "substitution" results from the replacement of one or more amino acids or nucleotides by different amino acids or nucleotides, respectively as compared to an amino acid sequence or nucleotide sequence of a naturally occurring polypeptide. The variant can have "conservative" changes, wherein a substituted amino acid has similar structural or chemical properties, e.g., replacement of leucine with isoleucine. More rarely, a variant can have "nonconservative" changes wherein a substituted amino acid does not have similar structural or chemical properties such as replacement of a glycine with a tryptophan.

In addition to creating a variant of the protein of interest, reduction or inhibition of expression of a protein that is expressed by the endothelial cell can be accomplished using known methods of genetic modification. For example, an endothelial cell expressing a leukocyte rolling mediator such as P-selectin can be genetically modified such that the expression of the P-selectin is reduced or inhibited using a homologous recombination gene "knock-out" method (see, for example, Capecchi, Nature, 344:105 (1990) and references cited therein; Koller et al., Science, 248:1227-1230 (1990); Zijlstra et al., Nature, 342:435-438 (1989), each of which is incorporated herein by reference; see, also, Sena and Zarling, Nat. Genet., 3:365-372 (1993), which is incorporated herein by reference). A "knock-out" of a target gene means an alteration in the sequence of the gene that results in a decrease of function of the target gene, preferably such that target gene expression is undetectable or insignificant. A knock-out of a gene means that function of the gene has been substantially decreased so that protein expression is not detectable or only present at insignificant levels. A "knock-in" of a target gene means an alteration in a host cell genome that results in altered expression or increased expression of the target gene, e.g., by introduction of an additional copy of the target gene, or by operatively inserting a regulatory sequence that provides for enhanced expression of an endogenous copy of the target gene.

The expression of the leukocyte migration mediator by an endothelial cell also can be reduced or inhibited by providing in the endothelial cell an antisense nucleic acid sequence, which is complementary to a nucleic acid sequence or a portion of a nucleic acid sequence encoding a leukocyte migration mediator. Methods for using an antisense nucleic acid sequence to inhibit the expression of a nucleic acid sequence are known in the art and described, for example, by Godson et al., J. Biol. Chem., 268:11946-11950 (1993), which is incorporated herein by reference.

Another embodiment creating control over the precise leukocyte migration mediators to be studied, including control over the type and amount of leukocyte migration mediator expressed, involves an embodiment of device 10 wherein at least one leukocyte migration mediator is disposed in channel 26 therein. For the purpose of clarity, the term "leukocyte migration mediator" used herein necessarily refers to at least one leukocyte migration mediator, unless otherwise specified. By disposing a leukocyte migration mediator in channel 26, it is possible to examine the ligand/receptor interactions underlying the leukocyte migration cascade, including the individual events of the cascade to gain a further understanding of this process. Disposing a leukocyte migration mediator in channel 26 also allows for the precise targeting of the ligand/receptor interactions underlying the individual events of the leukocyte migration cascade.

For example, in one embodiment, device 10 may be used to examine the capture of a leukocyte wherein the leukocyte migration mediator disposed in channel 26 may comprise a leukocyte capture mediator. As a consequence of the initial immune response to infection, inflammatory mediators induce the expression of adhesion molecules on the surface of the endothelium, resulting in an "activated endothelium." The first contact of a leukocyte with the activated endothelium is known as "capture" and is thought to involve a capture mediator P-selectin and a capture mediator binding partner L-selectin. P-selectin is thought to be the primary adhesion molecule involved the capture process and the binding of P-selectin to its main capture mediator binding partner, PSGL-1, is strongly implicated in this process. L-selectin has also been implicated in capture although its precise ligand on endothelial cells is unknown. Accordingly, in this embodiment of the present invention, the leukocyte capture mediator disposed in channel 26 may comprise, for example, P-selectin and/or an L-selectin binding ligand.

In another embodiment of the present invention, device 10 may be used to examine the rolling of a leukocyte wherein the leukocyte migration mediator may comprise a leukocyte rolling mediator. Once leukocytes are captured they may transiently adhere to the endothelium and begin to roll along the endothelium. The rolling of leukocytes is thought to involve: a rolling mediator, P-selectin; a rolling mediator binding partner, L-selectin; and a rolling mediator, E-selectin, although P-selectin is considered the primary adhesion molecule involved in this process. Accordingly, in this embodiment of the present invention, the leukocyte rolling mediator disposed in channel 26 may include, for example P-selectin, E-selectin, and/or an L-selectin ligand.

In another embodiment of the present invention, device 10 may be used to examine the arrest of a leukocyte wherein the leukocyte migration mediator may comprise a leukocyte arrest mediator. It is thought that most, if not all, leukocytes adhere to the endothelium only after having rolled along the endothelium. This adhesion, or "arrest" of the leukocytes on the top surface of the endothelium is initiated by chemoattractants such as IL-1 and TNF-α produced by cells at the injured site. These chemoattractants stimulate the endothelium to produce chemokines and arrest mediators on the surface of the endothelium opposite the basal lamina. The arrest mediators comprise, for example, integrin binding ligands such as ICAMs, including ICAM-1, ICAM-2, or/and ICAM-3 and VCAMs, including VCAM-1 and/or VCAM-2. The chemokines interact with chemokine receptors on the surface of the rolling leukocytes, which triggers the activation of arrest mediator binding partners on the surface of leukocytes. Arrest mediator binding partners include integrins, such as, for example, LFA-1, Mac-1, and p150,95, and VLA-4. Activation of these arrest mediator binding partners is thought to cause the slowly rolling leukocytes to "arrest" and strongly bind to the arrest mediators, such as ICAM-1, VCAM-1, and other integrin binding ligands such as collagen, fibronectin, and fibrinogen, on the endothelium. Accordingly, in this embodiment of the present invention, the leukocyte arrest mediator disposed in channel 26 may include at least one integrin binding ligand.

In yet another embodiment of the present invention, device 10 may be used to examine the transmigration of a leukocyte wherein the leukocyte migration mediator disposed in channel 26 comprises a leukocyte transmigration mediator. Once bound to the endothelium, the leukocytes flatten and squeeze between the endothelium to leave the blood vessel and enter the damaged tissue. The leukocytes follow a chemotactic gradient of chemoattractants released by cells in the damaged tissue area. Although much still remains unknown about transmigration, transmigration is thought to be mediated by platelets and endothelial cell adhesion molecule-1 (PECAM-1). Other potential transmigration mediators may be junctional adhesion molecule (JAM), ICAM-,1 VE-cadherin, LFA-1, IAP, VLA-4 and possibly CD99, a transmembrane protein. Accordingly, in this embodiment of the present invention, the leukocyte transmigration mediator disposed in channel 26 may include at least one of the aforementioned adhesion molecules or any other molecule determined to be implicated in transmigration.

Device 10 of the present invention may be used to study each aforementioned step in the leukocyte migration cascade in isolation, a combination of two or more steps in the leukocyte migration cascade, or the leukocyte migration cascade in its entirety. For example, if understanding and targeting rolling are desired, then preferably only leukocyte rolling mediators may be disposed in channel 26. If both rolling and arrest of leukocytes are desired to be studied, then both rolling and arrest mediators may be disposed in channel 26. If the entire leukocyte migration cascade is to be examined, then capture mediators, rolling mediators, arrest mediators, and transmigration mediators may be disposed in channel 26. It is understood that because certain molecules belong in more than one category of migration mediators (for example P selectin and an endothelial ligand binding L-selectin function as both capture mediators and rolling mediators) and because certain mediators may be present in conjunction (for example to study arrest, both rolling and arrest mediators may be present in channel 26 since direct adhesion from free-flowing leukocytes is thought to be extremely rare), certain steps, with the knowledge currently available, may not be monitored in isolation. Because much is still unknown about the specific details of the cascade of events occurring during the inflammatory response, this invention contemplates several methods of monitoring leukocyte migration in order to gain further understanding of the basic mechanisms controlling these events.

For example, to study the process of capture, a leukocyte migration mediator comprising a capture mediator is disposed in channel 26. A sample comprising leukocytes is introduced into channel 26 via first well 18 or second well 22. Capture events are defined as adhesive interactions of those freely flowing leukocytes moving closest to the surface of channel 26 containing the capture mediators and that are therefore the only leukocytes potentially capable of interacting with the capture mediators on channel 26. Different types of initial leukocyte capture can be characterized, observed, and monitored. For example, transient capture involving leukocytes only attaching briefly to channel 26 without initiating rolling motions, and rolling capture involving leukocytes that remain rolling on channel 26, can be determined. The number of each type of captured leukocyte can be divided by the total number of free flowing leukocytes to determine the frequency of initial capture of leukocyte.

The leukocytes can also be observed via any method known in the art and via methods disclosed in co-pending application entitled "Test Device and Method of Making Same," which is herein incorporated by reference in its entirety. Briefly, the leukocytes may be observed by using a microscope, including phase-contrast, fluorescence, luminescence, differential-interference contrast, dark field, confocal laser-scanning, digital deconvolution, and video microscopes; a high-speed video camera; and an array of individual sensors. For example, a digital movie camera may be used to monitor leukocyte activity under continuous flow conditions or a camera may be used to obtain still photographic images at particular points in time. Such observations reveal the interaction between the capture mediator binding partner expressed by the leukocytes and the capture mediator expressed by the endothelium. To detect such interaction, the cells may be incubated with staining agents and then detected based upon color or intensity contrast using any suitable microscopy technique(s). Alternatively, fluorescence-labeling may be used to detect whether capture mediator binding partners bind to capture mediators.

In another embodiment, non-labeled cells may be used to monitor migration. For example, a heterogeneous mixture of multiple cell types may be introduced into channel 26 with only one cell type capable of interacting with the capture mediators in channel 26. After the cells have been introduced into channel 26, an antibody specific to any antigen on the surface of this cell type may be used to label this cell type. If a multiple number of cell types can interact with the capture mediators, antibodies labeled with specific fluorophores can be used to distinguish different cell types.

In another embodiment directed to examining the process of rolling, a leukocyte migration mediator comprising a rolling mediator is placed in channel 26. A sample comprising leukocytes is introduced into channel 26 via first well 18 or second well 22. The number of leukocytes rolling and the rolling velocity of the leukocytes can be determined. In one embodiment, a camera is operatively linked to device 10 to obtain images of leukocytes rolling along channel 26 during predetermined intervals over a predetermined period of time. In this embodiment, the rolling velocity of the cells is determined by measuring the length the cells traveled ($1_{frame}$) in an image obtained by the camera and determining the exposure time of the image ($t_{exposure}$). To determine the rolling velocity (V), the following formula is used:

$$V = c(1_{frame}/t_{exposure})$$

where c is a conversion factor for determining the actual distance the cells have traveled. It may vary from image to image.

In another embodiment, several different assays utilizing different types of leukocytes are performed to characterize and compare the rolling velocities associated with the different cell types. In another embodiment, several different assays utilizing different rolling mediators are performed to characterize and compare the rolling velocites of cells associated with the different rolling mediators.

In another embodiment directed to examining the process of arrest, a leukocyte migration mediator comprising a first leukocyte migration mediator and a second leukocyte migration mediator, the first and second leukocyte migration mediators being different from one another is utilized. For the purpose of clarity, the term "first leukocyte migration mediator" used herein necessarily refers to at least one first leukocyte migration mediator and the term "second leukocyte migration mediator" used herein necessarily refers to at least one second leukocyte migration mediator. In this embodiment, the first leukocyte migration mediator comprising a rolling mediator and the second leukocyte migration mediator comprising an arrest mediator are placed in channel 26. A fluid sample comprising leukocytes is preincubated with a chemoattractant capable of triggering the activation of arrest mediator binding partners, for example, integrins, on the surface of the leukocytes. The chemoattractant is any suitable substance capable of triggering integrin expression by leukocytes and includes, for example, a formyl peptide, intercrines, IL-8 GRO/MGSA,NAP-2, ENA-78, MCP-1/MCAF, RANTES, I-309, other peptides, platelet activating factor (PAF), lymphokines, collagen, fibrin and histamines. The number of arrested cells can then be determined and assays similar to those performed with only rolling mediators can be performed.

In order to further understand the biological influences that underlie the leukocyte migration cascade, particularly the interaction between leukocytes and their counter-receptors on the endothelium, device 10 may also be used to analyze the effects of various test agents on the leukocyte migration cascade. These test agents may comprise any biological, chemical or electrical substance that includes, but is not limited to potential inhibitors of the leukocyte migration mediator or potential promoters of migration mediated by the leukocyte migration mediator. Further examples of such test agents include proteins, peptides, polypeptides, enzymes, hormones, lipids, carbohydrates, small molecules, and pharmaceutical agents. For example, the device may be used to identify an inhibitor or promoter that competitively or non-competitively inhibits or promotes a capture mediator and capture mediator binding partner interaction; rolling mediator and rolling mediator binding partner interaction; arrest mediator and arrest mediator binding partner interaction; and/or transmigration mediator and transmigration mediator binding partner interaction. As mentioned earlier, preferably the leukocyte migration mediator comprises a first leukocyte migration mediator and a second leukocyte migration mediator, the first and second leukocyte migration mediators beings different from one another. As such, in one embodiment, the test agent comprises a potential inhibitor of the first leukocyte migration mediator, the second leukocyte migration mediator, or both. In another embodiment, the test agent comprises a potential promoter of migration mediated by the first leukocyte migration mediator, the second leukocyte migration mediator, or both. After identifying inhibitors and promoters of the leukocyte migration cascade, these inhibitors and promoters can be tested for efficacy in vivo and ultimately utilized as therapeutic agents.

To screen a test agent that is a potential inhibitor of capture, a leukocyte migration mediator comprising a capture mediator is disposed in channel 26. After the potentially inhibitory test agent is incubated with a fluid sample comprising leukocytes, the sample is introduced into channel 26 via first well 18 or second well 22. Capture events are defined as adhesive interactions of those freely flowing leukocytes moving closest to the surface of channel 26 containing the capture mediators and that are, therefore, the only leukocytes potentially capable of interacting with the capture mediators on channel 26. Different types of initial leukocyte capture can be characterized, observed, and monitored. For example, transient capture involving leukocytes only attaching briefly to channel 26 without initiating rolling motions, and rolling capture involving leukocytes that remain rolling on channel 26 can be determined. The number of each type of captured leukocyte can be divided by the total number of free flowing leukocytes to determine the frequency of initial capture of leukocytes incubated with the potential inhibitory test agent and this frequency can be compared to the frequency of initial leukocyte capture in the absence of the potential inhibitory test agent. If the frequency of initial leukocyte capture is lower in the presence of the test agent relative to the frequency of initial leukocyte capture in the absence of the test agent, then the test agent is likely an inhibitor of leukocyte capture.

To screen a test agent that is a potential inhibitor of rolling, a leukocyte migration mediator comprising a rolling mediator is placed in channel 26. After the potentially inhibitory test agent is incubated with a fluid sample comprising leukocytes, the sample is introduced into channel 26 via first well 18 or second well 22. Alternatively, the potentially inhibitory test agent is introduced into the fluid sample during passage of the fluid sample in channel 26 when leukocytes have begun rolling. A decrease in rolling (e.g. as measured by a decrease in their velocity, or a decrease in the number of rolling leukocytes per volume) in the presence of the test agent, relative to that observed in the absence of the test agent, may indicate that the molecule is an inhibitor of capture and/or rolling.

To test a potentially inhibitory test agent of arrest, a leukocyte migration mediator comprising a first leukocyte migration mediator and a second leukocyte migration mediator, the first and second leukocyte migration mediators being different from one another may be utilized. In this embodiment, the first leukocyte migration mediator comprising a rolling mediator and the second leukocyte migration mediator comprising an arrest mediator are placed in channel 26. A fluid sample comprising leukocytes is preincubated with a chemoattractant capable of triggering the activation of arrest mediator binding partners, for example, integrins, on the surface of the leukocytes. After the fluid sample is preincubated with the potentially inhibitory test agent, the sample is introduced into channel 26 via first well 18 or second well 22. Alternatively, the potentially inhibitory test agent is introduced into the fluid sample during passage of the fluid sample in channel 26 when leukocytes have begun rolling. A decrease in arrest of the leukocytes (e.g., as measured by a decrease in the percentage of leukocytes that are arrested, or in the number of arrested leukocytes per volume) in the presence of the test agent relative to that observed in the absence of the test agent, indicates that the test agent may be an inhibitor of leukocyte arrest.

Device 10 can also be used to identify whether a test agent acts as a promoter of the inflammatory response by increasing the efficiency of the leukocyte migration cascade or by acting as a functional component thereof (e.g. a capture mediator, a rolling mediator, an arrest mediator, or a transmigration mediator). Such a functional component may be detected by its ability to promote capture, rolling, arrest or transmigration of a leukocyte where such action was previously lacking (due to lack of appropriate cellular specificity of a rolling mediator or arrest mediator previously present in channel 26 of chamber 14 or lack of any rolling mediator or arrest mediator). For example, device 10 comprising a first leukocyte migration mediator comprising a rolling mediator and second leukocyte migration mediator comprising an arrest mediator disposed in channel 26 may be used to identify an arrest mediator functional in leukocyte migration. In addition, device 10 comprising an arrest mediator and/or a rolling mediator disposed in channel 26 may be used to identify a rolling mediator functional in leukocyte migration.

To identify an arrest mediator, rolling mediators are disposed in channel 26 that have rolling binding partners present on the surface of leukocytes in a fluid sample to be introduced into channel 26 through first well 18 or second well 22. One or more chemoattractants capable of activating the leukocytes to express arrest mediator binding partners are preincubated with the fluid sample comprising leukocytes. A test agent to be tested for arrest mediating function is disposed in channel 26. After the fluid sample comprising leukocytes is introduced into channel 26 via first well 18 or second well 22 and the sample passes along channel 26, it is determined whether any leukocytes have arrested on channel 26. Arrest of leukocytes indicates that the test agent may be an arrest mediator that recognizes an arrest mediator binding partner on the surface of the same leukocytes that express the rolling mediator binding partner.

To identify a rolling mediator, the test agent to be tested for rolling mediator function is disposed in channel 26 and the fluid sample comprising leukocytes is introduced into channel 26 via the first well 18 or second well 22 and the sample is allowed to flow along channel 26. Rolling of the leukocytes along channel 26 indicates that the test agent has rolling mediator function and that the leukocytes express a binding partner for the rolling mediator. A rolling mediator is also identified by disposing the test agent to be tested for rolling mediator function in channel 26 and also disposing an arrest mediator in channel 26. One or more chemoattractants capable of activating the leukocytes to express arrest mediator binding partners, such as integrins, are preincubated with the fluid sample comprising leukocytes. The fluid sample comprising leukocytes is then introduced into channel 26 via the first well 18 or second well 22 and the sample is allowed to flow along channel 26. Arrest of leukocytes indicates that the test agent has rolling mediator function and that the leukocytes that express the arrest mediator binding partner and the chemoattractant receptor also express a binding partner for the test agent.

A test agent may also be identified as a functional component in the processes of leukocyte rolling or rolling and arrest, or an enhancer thereof, by the aforementioned methods in which an increase in number or percentage of leukocytes rolling or arrested is detected relative to the number or percentage of such leukocytes in the absence of the test agent. The migration of the leukocytes may be observed, monitored, recorded, and analyzed by any method known in the art and via the methods disclosed in co-pending application, "Test Device and Method of Making Same" referred to above.

The present invention also provides a kit to conduct the aforementioned assays. For example, the kit comprises a device including a housing 12 defining a plurality of chambers 14. Each of the plurality of chambers 14 includes a first well region 16 including at least one first well 18; a second well region 20 including at least one second well 22; and a channel region 24 including at least one channel 26 connecting the first well region 16 and the second well region 20 with another. The first well regions 16 and the second well regions 20 of the respective ones of the plurality of chambers 14 are preferably disposed relative to one another to match a pitch of a standard microtiter plate, thus advantageously allowing for high through-put screening of tests agents. The kit further includes a first leukocyte migration mediator. The kit may also contain a sample comprising leukocytes. The first leukocyte migration mediator and the sample comprising leukocytes may be packaged in the kit in any manner known in the art. For example, the first leukocyte migration mediator may be contained in a vial or container and the sample comprising leukocytes may similarly be contained in a separate vial or container. The kit may further include a second leukocyte migration mediator different from the first leukocyte migration mediator. The kit may additionally include an inhibitor adapted to inhibit the first leukocyte migration mediator, the second leukocyte migration mediator, or both. The kit may further include a promoter adapted to promote migration mediated by the first leukocyte migration mediator, the second leukocyte migration mediator, or both. The kit may also include any media and buffers necessary for use with the device and particular assays.

With respect to particular details of device 10, preferably, as shown by way of example in FIGS. 1 and 6, the housing 12 of device 10 comprises a support member 28, and a top member 30 mounted to the support member 28, wherein the support member 28 and the top member 30 are configured such that they together define the plurality of chambers 14. Preferably, the housing is also sized to match dimensions of a standard microtiter plate, for example, the dimensions of a 24-well microtiter plate, a 96-well microtiter plate, a 384-well microtiter plate, 768-well microtiter plate and a 1536-well microtiter plate. The top member may be made of any suitable material known in the art including glass, plastic, or an elastomeric material such as polydimethylsiloxane (PDMS). The support member may be made of glass, polystyrene, polycarbonate, polyacrylates, polymethyl methacrylate (PMMA), PDMS and other plastics. Preferably, top member 30 is in conformal contact with support member 28.

In another embodiment of the present invention, device 10 comprises a support member 28; and top member 30, the top member 30 mounted to the support member 28 by being placed in conformal contact with the support member 28. The support member 28 and the top member 30 are configured such that they together define at least one chamber 14. The at least one chamber 14 includes a first well region 16 including at least one first well 18; a second well region 20 including at least one second well 22; and a channel region 24 including at least one channel 26 connecting the first well region 16 and the second well region 20 with one another. In one embodiment, the at least one channel 26 includes at least one leukocyte migration mediator disposed therein. In another embodiment, the at least one channel 26 includes endothelial cells disposed therein. Preferably, the top member 30 is configured to be placed in reversible, conformal contact with the support member 28. As such, top member 30 is preferably made of a material that is adapted to effect conformal contact, preferably reversible conformal contact, with support member 28. According to this embodiment, the flexibility of such a material, among other things, allows top member 30 to form-fittingly adhere to support member 28 in such a way as to form a substantially fluid-tight seal therewith. The conformal contact should preferably be strong enough to prevent slippage of top member 30 on support member 28. Where the conformal contact is reversible, top member 30 may be made of a material having the structural integrity to allow top member 30 to be removed by a simple peeling process. This would allow top member 30 to be removed from support member 28 after experimentation, properly cleansed, and then reused for future assays. Preferably, the peeling process does not disturb any surface treatment, such as leukocyte migration mediators or endothelial cells, on support member 28. Additionally, the substantially fluid-tight seal effected between top member 30 and support member 28 by virtue of the conformal contact of top member 30 with support member 28 prevents fluid from leaking from one chamber to an adjacent chamber, and also prevents contaminants from entering the wells. The seal preferably occurs essentially instantaneously without the necessity to maintain external pressure. The conformal contact obviates the need to use a sealing agent to seal top member 30 to support member 28. Although embodiments of the present invention encompass use of a sealing agent, the fact that such a use is obviated according to a preferred embodiment provides a cost-saving, time-saving alternative, and further eliminates a risk of contamination of each chamber 14 by a sealing agent. Preferably, the top member 30 is made of a material that does not degrade and is not easily damaged by virtue of being used in multiple tests, and that affords considerable variability in the top member's configuration during manufacture of the same. More preferably, the material may be selected for allowing the top member 30 to be made using photolithography. In a preferred embodiment, the material comprises an elastomer such as silicone, natural or synthetic rubber, or polyurethane. In a more preferred embodiment, the material is PDMS. Support member 28 provides a support upon which top member 30 rests, and may be made of any material suitable for this function. Suitable materials are known in the art such as glass, polystyrene, polycarbonate, PMMA, polyacrylates, PDMS, and other plastics.

With respect to portions of chamber 14, in one embodiment, well regions 16 and 20 are vertically offset with respect to one another is a test orientation of device 10. In a preferred embodiment, well regions 16 and 20 are horizontally offset with respect to one another is a test orientation of device 10. Wells 18 and 22 of respective well regions 16 and 20 of each chamber 14 are not limited in their configuration to any particular three dimensional contour, it being only required that they be adapted to receive a fluid therein, preferably a sample comprising leukocytes. Preferably, wells 18 and 22 are configured such that they substantially define circles in top plan views thereof, as shown by way of example in FIGS. 1-6. However, other contours in the top plan view of a given well is within the scope of the present invention, as readily recognized by one skilled in the art. Where the wells define circles in top plan views thereof, and where, the well regions are disposed relative to one another to match a pitch of a standard 96-well microtiter plate, the pitch P is set to be equal to about 9 mm, and the diameter $D_w$ of a top plan contour of the wells is set to be equal to about 6 mm. In such a case, length L of each channel 26 is equal to about 3 mm. As shown in particular in FIG. 2, wells 18 and 22 are defined in part by respective through-holes 18$^1$ and 22$^1$ in top member 30, and in part by an upper surface U of support member 28. In particular, the sides of each well 18 and 22 are defined by respective walls of the through holes 18$^1$ and 22$^1$ in the top member 30, and the bottoms of wells 18 and 22 are defined by a corresponding portion of the upper surface U of support member 28.

Figure 2:
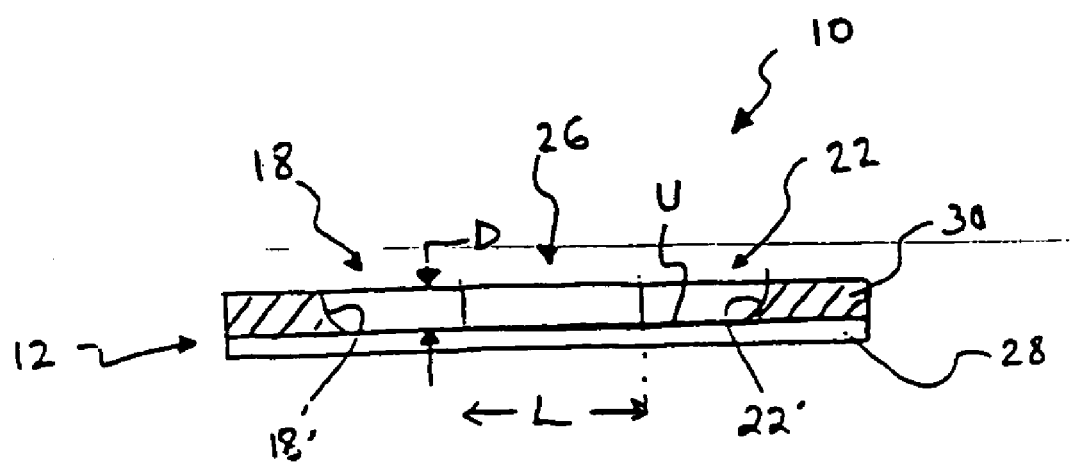
FIG. 2 is a cross-sectional view of the device of FIG. 1 along lines II-II.

With respect to channel region 24 of chamber 12, as seen collectively in FIGS. 2-4, a length L of a channel 26 is defined in a direction of the longitudinal axis thereof. In addition, depth D of a channel 26 is defined in a direction normal to a top surface of housing 12; and a width W of a channel region 26 is defined in a direction normal to length L and depth D. Preferably, channel region 24 comprises a plurality of rectilinear, parallel channels 26 extending between well regions 16 and 20. Preferably, channels 26 have lengths L that are substantially identical, as shown schematically by way of example in FIG. 4. More preferably, the plurality of channels 26 comprises eight channels. By using multiple channels, multiple assays can be performed simultaneously using one sample comprising leukocytes. In such an embodiment, all assays are performed under uniform and consistent conditions and therefore provide statistically more accurate results. Channels 26 preferably each have a width W of 50 μm to 5 mm; a length L of about 1-10 mm; and a height H of about 10-100 μm. More preferably, the channels 26 each have a width W of about 100 microns, a length L of about 3 mm and a height of about 50 μm to about 80 μm. The dimensions of the channels 26 of channel region 24 should be configured to support the migration of leukocytes under conditions simulating such migration during an inflammatory response. As such, the channel region should be adapted to support the migration of leukocytes under shear flow and to support at least one leukocyte migration mediator disposed therein. It is to be noted that the embodiments of device 10 described in relation to FIGS. 1-6 are merely exemplary, and that various other configurations are within the scope of the present invention. Other examples for the configuration of device 10 are provided in the co-pending application entitled "Test Device and Method of Making Same," referenced to above.

Device 10 of the present invention can be fabricated, according to a preferred embodiment of a method of the present invention, by standard photolithographic procedures. Photolithographic procedures can be used to produce a master that is the negative image of any desired configuration of top member 30. For example, the dimensions of chamber 14, such as the size of well region 16 and 18, or the length of channel region 24, can be altered to fit any advantageous specification. Once a suitable design for the master is chosen and the master is fabricated according to such a design, the material for top member 30 is either spin cast, injected, or poured over the master and cured. Once the mold is created, this process can be repeated as often as necessary. This process not only provides great flexibility in the top member's design, it also allows the top members to be massively replicated.

Once the device is fabricated, leukocyte migration mediators can be disposed in channel 26. The leukocyte migration mediators can be disposed in channel 26 by affixing them or physioadsorbing them directly on the upper surface U of support member 28, or by coating a solution or suspension comprising the leukocyte migration mediators on the upper surface U of support member 28, as long as the mediators are accessible to leukocytes flowing by the upper surface U. In one embodiment, the leukocyte migration mediators are either covalently or non-covalently affixed directly to upper surface U by techniques such as covalent bonding via an amide, ester or lysine side chain linkage or adsorption. Other method of disposing leukocyte migration mediators, including immobilizing them on upper surface U of support member 28 are disclosed in co-pending application, "Test Device and Method of Making Same" referred to above.

The present invention also provides a device comprising a housing 12; means associated with the housing defining a plurality of chambers 14 in the housing 12. Each of the plurality of chambers 14 includes: an inlet means for receiving a sample comprising leukocytes; an outlet means in flow communication with the inlet means for receiving the sample comprising leukocytes from the inlet means; and connection means connecting the inlet means and the outlet means to one another, the connection means including at least one leukocyte migration mediator disposed therein. An example of means associated with the housing defining a plurality of chambers in the housing comprises a top member mounted to a support member as shown in FIG. 6. The above means have been substantially shown and described in relation to the embodiments of the FIGS. 1-6. Other such means would be within the knowledge of persons skilled in the art.

In another embodiment, the present invention provides methods of assaying and studying biological phenomenon that either depend on or react to gradient formation and/or flow conditions. Such biological phenomenon include many of the processes in the body such as cell-surface interactions such as that occurring during leukocyte adhesion and rolling. In addition, studies involving chemotaxis, haptotaxis and cell migration will be better served with assays that are able to study such cell movement in the presence of gradients and/or flow conditions.

Various types of gradients are useful in the study of biological systems. Such useful gradients include static gradients, which have concentrations that are fixed, or set or substantially fixed or set. One example of a static gradient is a gradients of immobilized molecules on a surface. Non-limiting examples of static gradients include the use of differing concentrations of immobilized biomolecules (proteins, antibodies, nucleic acids, and the like) or immobilized chemical moieties (drugs and small molecules). Other useful gradients include dynamic gradients, which have concentrations that may be varied. One example of a dynamic gradient is a gradient of fluid streams having molecules in varying concentrations. Non-limiting examples of fluid gradients include the use of fluid streams containing biomolecules such as growth factors, toxins, enzymes, proteins, antibodies, carbohydrates, drugs or other chemical and small molecules in varying concentrations.

In one embodiment of the present invention, a dynamic/solution based gradient is created by laminar flow technology. Laminar flow technology typically involves two or more fluid streams from two or more different sources. These fluid streams are brought together into a single stream and are made to flow parallel to each other without turbulent mixing. Fluids with different characteristics such as varying low Reynolds numbers will flow side by side and will not mix in the absence of turbulence. Since the fluids do not mix, they create pseudo-channels (pseudo by the fact that there are no physical separation between the fluids). The generation of solution and surface gradients is discussed in U.S. patent application 2002/

0113095 and an article, Jeon, Noo Li, et al., *Langmuir*, 16, 8311-8316 (2000). Both of these references are herein incorporated by reference in their entirety.

Figure 13:
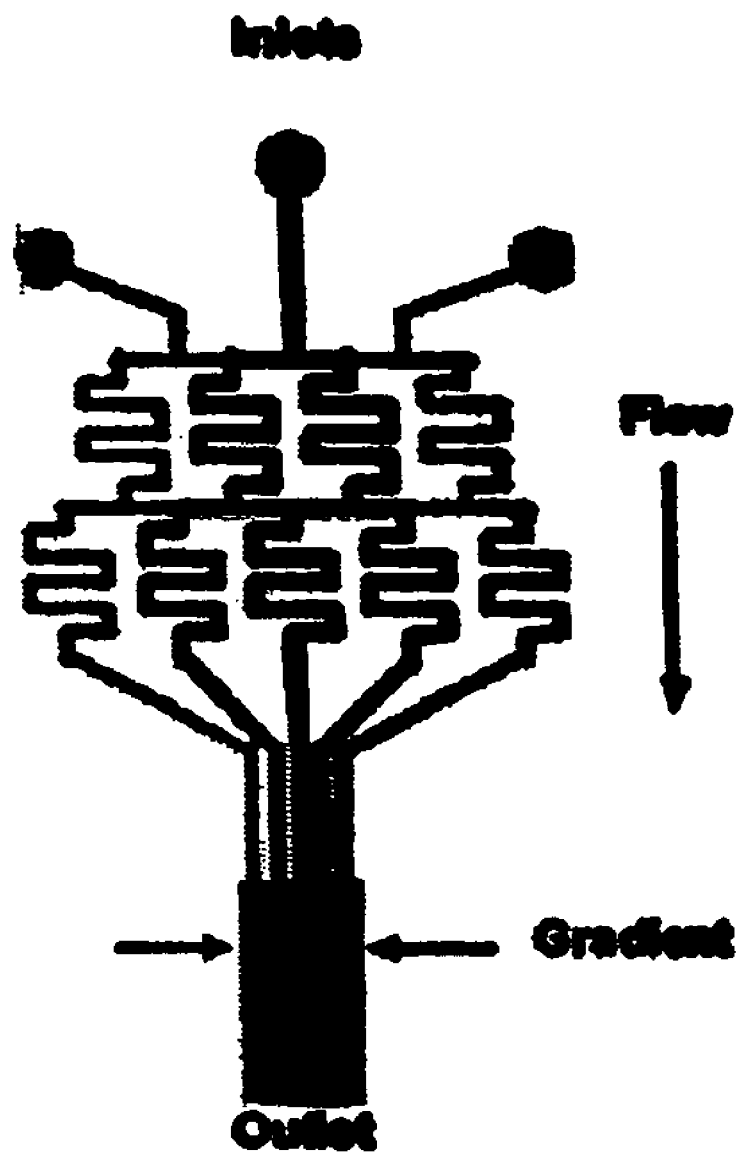
FIG. 13 depicts an exemplary microfluidic device for creating a laminar flow gradient.

In these references a PDMS microfluidic device was used to generate a gradient through a microfluidic network of capillaries. Solutions containing different chemicals were introduced into three separate inlets and allowed to flow through the network of capillaries. The fluid streams were repeatedly combined, mixed, and split to yield distinct mixtures with distinct compositions in each of the branching channels. As illustrated in FIG. 13, when all of the branches were recombined, a concentration gradient was established across the outlet channel, perpendicular to the flow direction.

By combining the devices of the present invention with the formation of a dynamic gradient, a vast number of assay parameters can be generated by altering any portion of the device. For example, by combining the device as disclosed herein with cell patterning techniques, along with the introduction of a dynamic gradient, various conditions can be created to test numerous biological interactions. Further, the device and assays may be useful in drug discovery and drug testing as many cells and biological materials behave differently ex vivo when not exposed to gradients than compared to when the cells or biological materials are present in vivo and thus exposed to gradients and flow conditions.

Accordingly, in one embodiment of the present invention, cells can be patterned across channel 26. Cell patterning can be achieved by methods known in the art, as well as disclosed in the present invention (such as, but not limited to, microcontact printing or by the use of elastomeric stencils). A solution containing any desired biomolecule or chemical/drug can then be flowed across the patterned cells. Additionally, the cells could be first treated by a biomolecule such as an activator to more closely recreate a biological system, and then be subsequently exposed to a chemical or drug. By creating a gradient, such as by laminar flow, different amounts of biomolecules or chemicals/drugs can be delivered to the patterned cells and thus the effect of concentration of each biomolecule or chemical/drug be tested simultaneously against each other. This side by side, same time comparison thus reduces the variability of assay to assay conditions.

Creating dynamic gradients with laminar flow in combination with the devices of the present invention provides numerous assay configurations. For example, by varying the combinations of the cells on the surface, the biomolecule in channels 26 and the compounds in channel 26, one can create a vast multitude of assays.

With respect to immobilized cells or other immobilized biomolecules such as proteins, antibodies, nucleic acids, etc. different assay configurations are possible. In one embodiment, a single type of cell is immobilized throughout the entire channel region 24. In another embodiment, a mixture of cell types are immobilized, one cell type per region 24. In another embodiment, a mixture of cell types is immobilized throughout the entire channel region 24. This may be advantageous in monitoring cell-cell interactions. In yet another embodiment, different cell types are immobilized in each different region 24.

In addition to the various immobilization schemes, further assay design flexibility centers around the leukocyte migration mediators or other biomolecules present in channels 26. For example, in one embodiment, one type of leukocyte migration mediator is present in each channel 26 at the same concentration. In another embodiment, one type of leukocyte migration mediator is present in each channel 26 at differing concentrations. In another embodiment, different leukocyte migration mediators are present in each channel 26. In another embodiment, there is a mixture of leukocyte migration mediators in each channel 26. Each channel 26 may have the same mixture or a different mixture. When the mixture is the same, the ratios or concentrations of the different leukocyte migration mediators may be different in each channel 26.

Likewise with respect to compounds, such as drugs or test substances, the present invention provides flexibility in assay design. For example, in one embodiment a single compound is present in all channels 26 at the same concentration throughout. In another embodiment, the same compound is present in all the channels 26 but each channel 26 has a different concentration of that compound. In another embodiment, each channel 26 has a different compound. In another embodiment, there is more than one compound. When there is more than one compound, each channel 26 may have the same mixture of compounds or may have a different mixture of compounds. Further, when the mixtures of the compounds are the same, each channel 26 may receive a different concentration of that mixture. Yet, even further, each channel 26 may receive the mixture of the compounds, with each channel 26 having a different ratio of compounds to each other.

Such assay systems can be used to test among many numerous biological interactions, the effects of chemical or drugs on cells or other biomolecules. For example, one may use the device and the assays of the present invention to measure the IC50 of a compound by using a laminar flow gradient of a compound present from a low concentration to a high concentration flowed across immobilized biomolecules.

Throughout this application, reference has been made to various publications, patents, and patent applications. The teachings and disclosures of these publications, patents, and patent applications in their entireties are hereby incorporated by reference into this application to more fully describe the state of the art to which the present invention pertains.

EXAMPLES

I. Procedure for Fabrication of the Device for Monitoring Leukocyte Migration

A master of the device according to the present invention is made using photolithography. A silicon substrate is patterned based on a negative pattern of the top member using a suitable photoresist. Thereafter, polydimethyl siloxane (PDMS) is poured on top of the master and placed under vacuum in order to extract air bubbles therefrom. The thus poured PDMS layer is allowed to cure in an oven at about 30° C. for about 17 hours. Thereafter, the device is washed thoroughly with 2% Micro-90 (a product of International Products Corp.), rinsed for 10 minutes at 70° C. in "Sonic Bath," and rinsed with de-ionized water, followed by a rinsing with 100% ethanol. The PDMS layer is then dried under nitrogen. At the same time, a pre-cleansed glass slide, such as a rectangular one having dimensions of about 4.913+/−0.004 inches (in.) by about 3.247+/−0.004 in. and a thickness of about 1.75 millimeters (mm), mm, is washed three times with ethanol and twice with methanol. Preferably, the surfaces of the PDMS layer and the glass slide to be bound together are both plasma oxidized for about 84 seconds. The PDMS layer and the glass slide are then pressed together using forceps to squeeze out air pockets therebetween. In this manner, a fluid-tight, conformal contact is established between the PDMS layer as top member and the glass slide as support member. In addition, by virtue of PDMS having been used as the top member material, the conformal contact between the PDMS layer and the glass slide is reversible.

It is to be noted that the method of making the device of the present invention described above is merely an example.

Other examples for the method of making the device are provided in the co-pending application entitled "Test Device and Method of Making Same" referred to above.

II. Leukocyte Migration Assay Utilizing Device of the Present Invention with a Rolling Mediator Disposed in a Channel Therein A. Isolation of Leukocytes Neutrophils are isolated from a volume of 5 milliliters (ml) of human blood from a healthy volunteer. The 5 ml of blood is diluted with Hanks Balance Salt Solution (HBSS) in a 1:2 ratio thereby increasing the total volume of blood to equal 15 ml. The whole blood dilution is layered over 10 ml of Ficoll-Paque Plus (obtained from Amersham Pharmacia Biotech AB, catalog # 17-1440-02). The blood is then centrifuged for 30 minutes at 400 g at room temperature. The supernatant is aspirated off without disturbing the pellet. The pellet is resuspended on 10 ml of HBSS and 150 µl of 6% dextran to make up a 1% solution. The red blood cells are allowed to settle for at least one hour at room temperature. The neutrophils remain inside the supernatant while the red blood cells mostly settle down forming a pellet. The supernatant is pipetted out and diluted in a 1:2 ratio using HBSS. This suspension is centrifuged for 10 minutes at a velocity of 600 g. The supernatant is aspirated and the pellet is dissolved in 19 ml of deionized water. After one minute, the pellet is resuspended in 1 ml of 10×PBS. This suspension is centrifuged at 400 g for 10 minutes. The red blood cells are lysed in this process and the remaining cells are mostly neutrophils. The resulting pellet may be dissolved in media containing BSA in order to avoid the clumping of cells after a prolonged period of time at room temperature. The cell density is determined by counting the number of cells using a hemocytometer.

B. Placement of Leukocytes and Leukocyte Migration Mediators in Chamber

Figure 7:
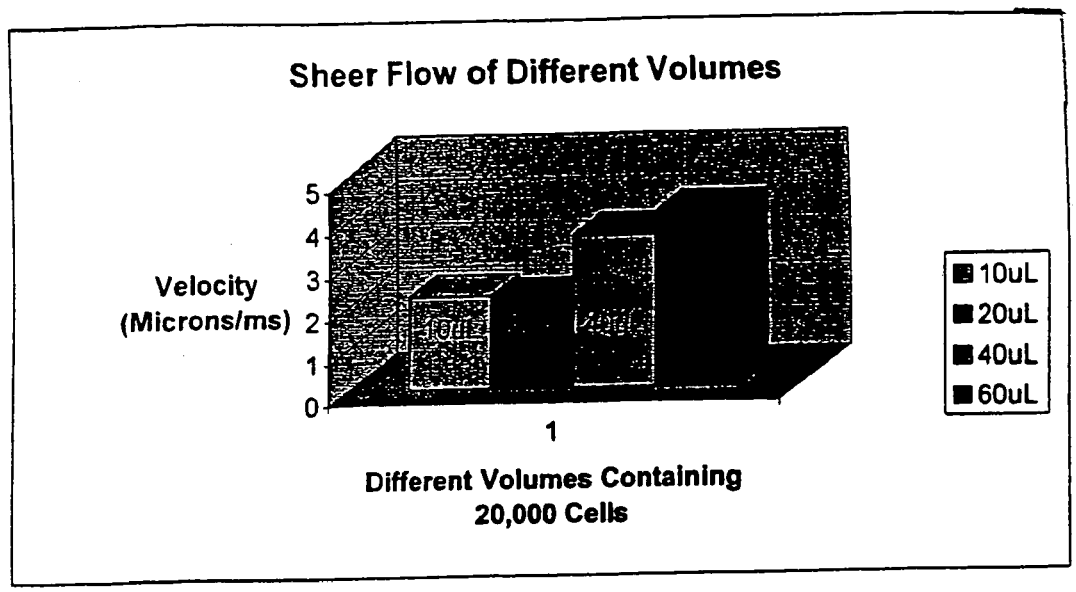
FIG. 7 is a bar graph comparing the velocity of shear flow under different cell suspension volumes.

20 µl of water are pipetted in the first well of the chamber of the device fabricated according to the method disclosed in Section I and microcapillary action draws the water into the channel. After ensuring no air bubbles are inside the channel, an additional 10 µl of water are pipetted in the second well of the chamber. After 15 minutes pass and the hydrostatic pressure equalizes, 10 µl of P-Selectin at a concentration of 50 µg/mL (obtained from R&D Systems, catalog #ADP3) is pipetted in both wells. The device is incubated for two hours at room temperature in a dish with a cover in order to keep the wells from drying out. After the incubation, the channel is washed four times using 0.1% Bovine Serum Albumin (BSA) in Phosphate Buffer Saline (PBS). After this last wash, all the liquid inside the wells is pipetted out leaving only liquid in the channel. 20 µl of 0.1% BSA in PBS is added to the first well and 10 µl of BSA in PBS is added to the second well. After 15 minutes pass and the hydrostatic pressure equalizes, neutrophils obtained from the method described in part A in 60 µl of media are added to the first well of each chamber (about $10^3$ to about $10^6$ cells per well of a 24 well plate, in volume of 60 µl of media per well) (non-labeled and fluorescently labeled monocytic cell lines-U937 (obtained from ATCC, catalog # TIB-202 and THP-1 (obtained from ATCC, catalog # CRL-1593.2) as well as other primary leukocytes may also be used. As seen in FIG. 7, it is preferred that 40 µl-60 µl of media be used to generate the range of flow velocity under normal physiological conditions (about 0.1 dynes/cm² to about 20 dynes/cm²).

C. Data Acquisition

Digital images are taken on a Zeiss inverted microscope using AXIOCAM™ beginning 15 seconds after the sample comprising leukocytes is added to the first well. Data is analyzed on AXIOVISION™ software. Time-lapsed images are taken every 30 seconds for 5 minutes and 15 seconds. 10× objective lens is used to view and record the number of cells rolling along the channel.

D. Determining the Rolling Velocity of the Leukocytes

In order to characterize the rolling velocity of the leukocytes at a particular time, an image obtained using the method described in part C is used measure the distance the leukocytes traveled during the exposure time of the image. To determine rolling velocity (V), the following formula is used:

$$V = c(1_{time}/t_{exposure}) \text{ where}$$

c: conversion factor for determining the actual distance the cells traveled.

This factor may vary from image to image.

$1_{time}$: the length of the leukocytes migration in the captured image.

$t_{exposure}$: the exposure time of the image.

Preferably $t_{exposure}$ is 100 milliseconds (ms) when the flow rate is about 0.1 dynes/cm² to about 20 dynes/cm².

III. Leukocyte Migration Assay Utilizing Device of the Present Invention with a Rolling Mediator and Arrest Mediator Disposed in a Channel Therein A. Isolation of Leukocytes Neutrophils are isolated according to the method disclosed in section II, part A.

B. Placement of Leukocytes and Leukocyte Migration Mediators in Chamber

20 µl of water are pipetted in the first well of the chamber of the device fabricated according to method disclosed in section I. Microcapillary action draws the water into the channel. After ensuring no air bubbles are inside the channel, an additional 10 µl of water are pipetted in the second well of the chamber. After 15 minutes pass and the hydrostatic pressure equalizes, 10 µl of P-Selectin with a concentration of 50 µg/mL (obtained from R&D Systems, catalog #ADP3) is pipetted in the first well and 10 µl of ICAM-1 with a concentration of 50 µg/mL (obtained from R&D Systems) is simultaneously pipetted in the second well. The device is incubated for two hours at room temperature in a dish with a cover in order to keep the wells from drying out. After the incubation, the channel is washed four times using 0.1% Bovine Serum Albumin (BSA) in Phosphate Buffer Saline (PBS). After this last wash, all the liquid inside the wells is pipetted out leaving only liquid in the channel. 20 µl of 0.1% BSA in PBS is added to the first well and 10 µl of BSA in PBS is added to the second well. After 15 minutes pass and the hydrostatic pressure equalizes, neutrophils isolated from part A in 60 µl of media are added to the first well of each chamber (about $10^3$ to about $10^6$ cells per well of a 24 well plate, in volume of 60 µl of media per well) (non-labeled and fluorescently labeled monocytic cell lines-U937 and THP-1 as well as primary leukocytes may also be used). As seen in FIG. 7, it is preferred that 40 µl-60 µl of media be used to generate the range of flow velocity under normal physiological conditions (about 0.1 dynes/cm² to about 20 dynes/cm²).

C. Data Acquisition

Digital images are taken on a Zeiss inverted microscope using AXIOCAM™ beginning 15 seconds after the sample comprising leukocytes is added to the first well. Data is analyzed on AXIOVISION™ software. Time-lapsed images are taken every 30 seconds for 5 minutes and 15 seconds. 10× objective lens is used to view and record the number of cells rolling along the channel and adhering to the channel.

IV. Leukocyte Migration Assay Utilizing Confluent Layers of Endothelial Cells

A. Isolation of Leukocytes

Neutrophils are isolated according to the method disclosed in section II, part A.

B. Placement of Leukocytes and Endothelial Cells in Chamber

10 µL of a 10× dilution of MATRIGEL™ (obtained from BD Bioscience, catalog # 356231) is added to the first well of the device fabricated according to the method disclosed in Section I. 10 µL are added to the first well and the microcapillary action draws the solution into the channel. The MATRIGEL™ is then allowed to gel for about 15 minutes at room temperature. Another option is to coat the channel with 1 mg/mL concentration of fibronectin (obtained from Gibco-BRL, catalog # 33016-015) that is obtained by diluting the stock concentration of fibronectin using a 0.1% BSA solution. 5 µL of fibronection at a concentration of 1 mg/mL are pipetted into the first well and microcapillary action draws the solution in to the channel.

Once the channel has been coated with either MATRIGEL™ or fibronectin, the endothelial cells are prepared for seeding. Cells are obtained from Clonetics at Bio-Whittaker in cryogenic vials. They are grown in T75 flasks until ready to be split using 0.025% Trypsin/EDTA. The cells are seeded on the channel at a density of $1 \times 10^5$ cells per 5 µl of media per assay for approximately two days to form a confluent monolayer of endothelial cells. During these two days, the endothelial cells are replenished with 40 µL of fresh media added into each well. After approximately two days, the endothelial cells are exposed to a concentration of 1 ng/ml of TNF-α (other chemokines may alternatively be used) for a period of four hours at 37° C. At the end of the four hours, the TNF-α is washed using 60 µL of fresh media twice. The volume of media inside each well is replaced with 15 µL of fresh media. Neutrophils isolated from Section II, part A in 60 µl of media are added to the first well of chamber the (about $10^3$ to about $10^6$ cells per well of a 24 well plate, in volume of 60 µl of media per well) (non-labeled and fluorescently labeled monocytic cell lines-U937 and THP-1 as well as primary leukocytes may also be used.) If a monocytic cell line is used, the cells are fluorescence labeled using cell tracker probes (obtained from Molecular Probes, catalog #s C-2925 and C-2927). The cells are incubated with a 1 µM concentration of probes for 30 minutes at 37° C. The media is then changed and the cells are placed inside an incubator for an additional 30 minutes.

As seen in FIG. 7, it is preferred that 40 µL-60 µL of media be used to generate the range of flow velocity under normal physiological conditions (about 0.1 dynes/cm² to about 20 dynes/cm²).

C. Data Acquisition

Digital images are taken on a Zeiss inverted microscope using AXIOCAM™ beginning 15 seconds after the sample comprising leukocytes is added to the first well. Data is analyzed on AXIOVISION™ software. Time-lapsed images are taken every 30 seconds for 5 minutes and 15 seconds. 10× objective lens is used to view and record the number of cells rolling along the channel.

D. Determining the Rolling Velocity of the Leukocytes

In order to characterize the rolling velocity of the cells at a particular time, an image obtained from the method described in part C is used to measure the distance the leukocytes traveled during the exposure time of the image. To determine rolling velocity (V), the following formula is used:

$$V = c(1_{time}/t_{exposure}) \text{ where}$$

c: conversion factor for determining the actual distance the cells traveled.

This factor may vary from image to image.

$1_{time}$: the length of the leukocytes migration in the captured image.

$t_{exposure}$: the exposure time of the image.

Preferably $t_{exposure}$ is 100 ms when the flow rate is about 0.1 dynes/cm² to about 20 dynes/cm².

V. Inhibition of Leukocyte Migration Assay Utilizing Device of the Present Invention With a Rolling Mediator and an Arrest Mediator Disposed in a Channel Therein A. Isolation of Leukocytes Neutrophils are isolated according to the method disclosed in section II, part A.

Figure 8:
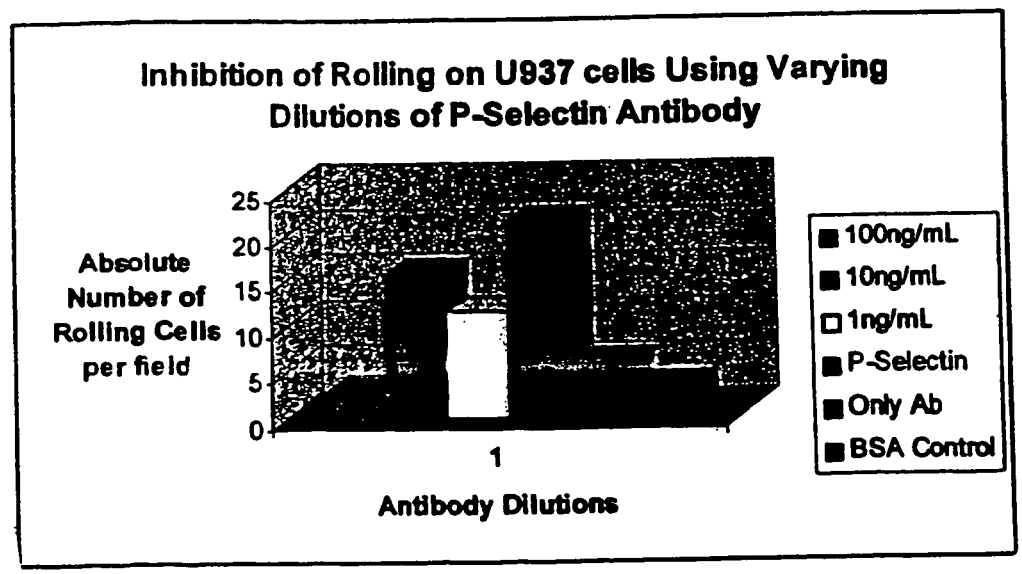
FIG. 8 is a graph comparing the number of cells rolling under different dilutions of P-selectin antibody.
Figure 9:
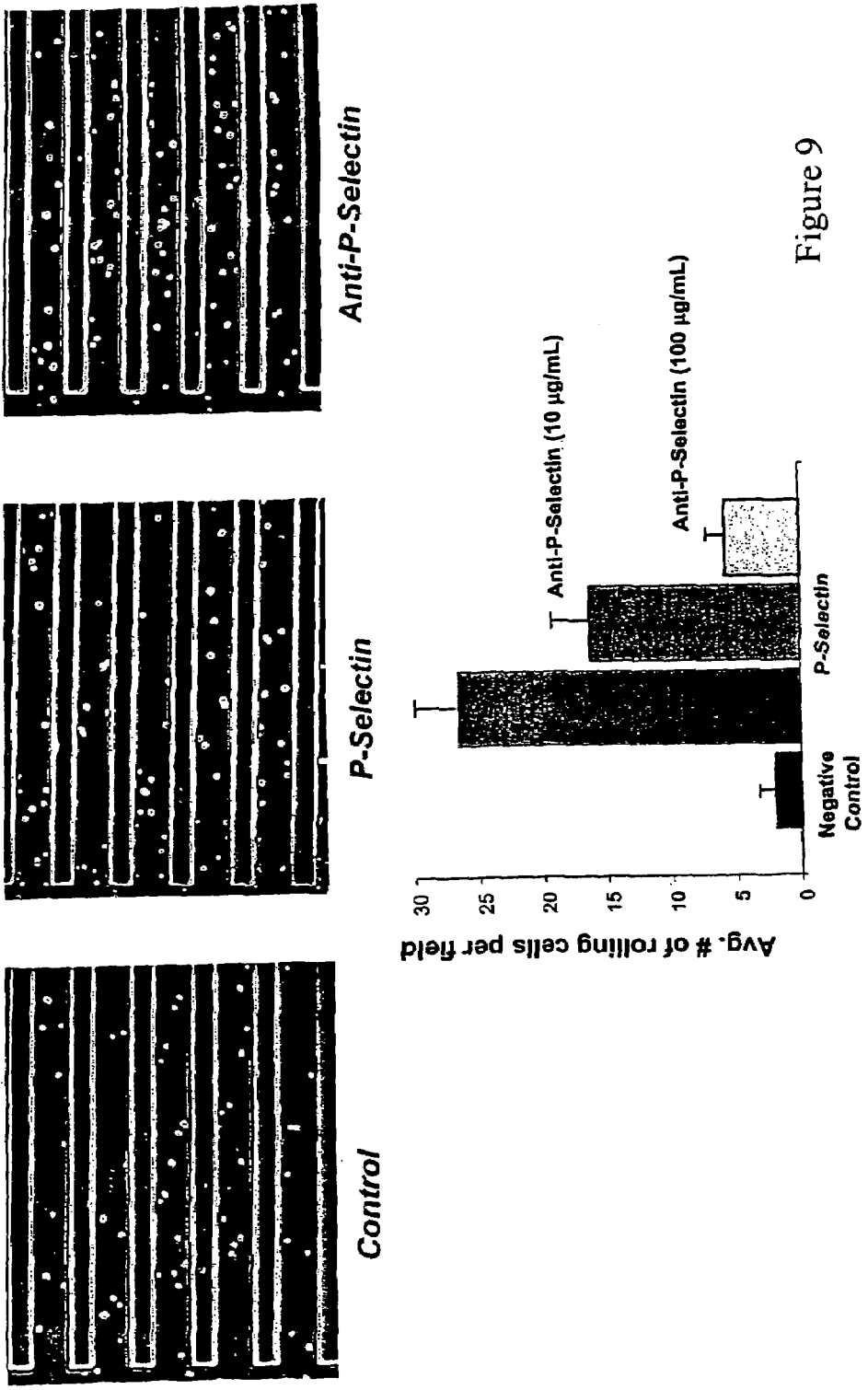
FIG. 9 is a graph and time-lapsed still photographs of cells rolling and adhering under different dilutions of P-selectin antibody.

B. Placement of Leukocytes, P-selectin, and P-selectin Antibodies in the Chamber With respect to five chambers, 20 µl of 0.1% BSA are pipetted in the first well of each chamber of the device fabricated according to the method described in Section I. Microcapillary action draws water into the channels. After ensuring no air bubbles are inside the channels, an additional 10 µl of BSA are pipetted in the second well of each chamber. After 15 minutes pass and the hydrostatic pressure equalizes, 10 µl of P-Selectin (50 µg/mL) are pipetted in first wells and 10 µl of ICAM-1 (50 µg/mL) are pipetted into the second wells using a multipipettor. The device is incubated for two hours at room temperature in a dish with a cover in order to keep the wells from drying out. After the incubation, the channels of each well are washed four times using 0.1% Bovine Serum Albumin (BSA) in Phosphate Buffer Saline (PBS). With respect to the five different chambers, 100 ng/mL of P-selectin antibody is pipetted into the first well of chamber #1; 10 ng/mL of P-selectin antibody is pipetted into first well of chamber #2; and 1 ng/mL of P-selectin antibody is pipetted into the first well of chamber #3; 100 µg/mL of P-selectin antibody is pipetted into the first well of chamber #4; and 0.1% BSA in PBS is pipetted into the first well of chamber #5. The device is incubated for thirty minutes at room temperature in a dish with a cover in order to keep the wells from drying out. After incubation, the channels are washed first with 20 µl of BSA, then with 10 µl of BSA and then 0.1% BSA in PBS. Neutrophils in 20 µl of media are added to the first well of each chamber (about $10^3$ to about $10^6$ per well of a 24 well plate, in volume of 20 µl of media per well) (non-labeled and fluorescently labeled monocytic cell lines-U937 and THP-1 as well as primary leukocytes may be used). Digital images are taken on a Zeiss inverted microscope using AXIOCAM™ beginning 15 seconds after the sample comprising leukocytes is added to the first well. Data is analyzed on AXIOVISION™ software. Time-lapsed images are taken every 30 seconds for 5 minutes and 15 seconds. 10× objective lens is used to view and record the number of cells rolling after the treatment with P-selectin antibody. As seen from FIGS. 8 and 9, a 100 ng/mL dilution of the antibody is a preferred concentration to inhibit the rolling of the cells. As seen from the still photo images of FIG. 9, the number of leukocytes that roll and adhere to the endothelium are reduced in the presence of anti-P selectin.

C. Placement of Leukocytes, E-Selectin, and E-Selectin Antibodies in the Chamber With respect to five chambers, 20 µl of 0.1% BSA are pipetted in the first well of each chamber of the device fabricated according to the method described in Section I. Microcapillary action draws the BSA into the channels. After ensuring no air bubbles are inside the channels, an additional 10 µl of 0.1% BSA are pipetted in the second well of each chamber. After 15 minutes pass and the hydrostatic pressure equalizes, 10 μl of E-Selectin (50 μg/mL) are pipetted in the first wells and 10 μl of ICAM-1 (50 μg/mL) are pipetted into the second wells using a multipipettor. The device is incubated for two hours at room temperature in a dish with a cover in order to keep the wells from drying out. After the incubation, the channels of each well are washed four times using 0.1% Bovine Serum Albumin (BSA) in Phosphate Buffer Saline (PBS). With respect to the five different chambers, 100 ng/mL of E-selectin antibody is pipetted into the first well of chamber #1; 10 ng/mL of E-selectin antibody is pipetted into first well of chamber #2; and 1 ng/mL of E-selectin antibody is pipetted into the first well of chamber #3; 100 μg/mL of E-selectin antibody is pipetted into the first well of chamber #4; and 0.1% BSA in PBS is pipetted into the first well of chamber #5. The device is incubated for thirty minutes at room temperature in a dish with a cover in order to keep the wells from drying out. After incubation, the channels are washed four times with 0.1% BSA in PBS. Neutrophils in 20 μl of media are added to the first well of each chamber (about $10^3$ to about $10^6$ cells per well of a 24 well plate, in volume of 20 μl of media per well) (non-labeled and fluorescently labeled monocytic cell lines-U937 and THP-1 as well as primary leukocytes may be used). Digital images are taken on a Zeiss inverted microscope using AXIOCAM™ beginning 15 seconds after the sample comprising leukocytes is added to the first well. Data is analyzed on AXIOVISION™ software. Time-lapsed images are taken every 30 seconds for 5 minutes and 15 seconds. 10× objective lens is used to view and record the number of cells rolling after the treatment with E-selectin antibody. As seen from FIG. 10, a 100 ng/mL dilution of the antibody is a preferred concentration to inhibit the rolling of the cells. As seen from the still photo images of FIG. 10, the number of leukocytes that roll and adhere to the endothelium are reduced in the presence of anti-E selectin.

VI. Inhibition of Leukocyte Migration Assay Utilizing Device of the Present Invention with Confluent Layers of Endothelial Cells Disposed in a Channel Therein A. Isolation of Leukocytes Neutrophils are isolated according to the method disclosed in section II, part A.

B. Placement of Leukocytes and Endothelial Cells in Chamber

Figure 10:
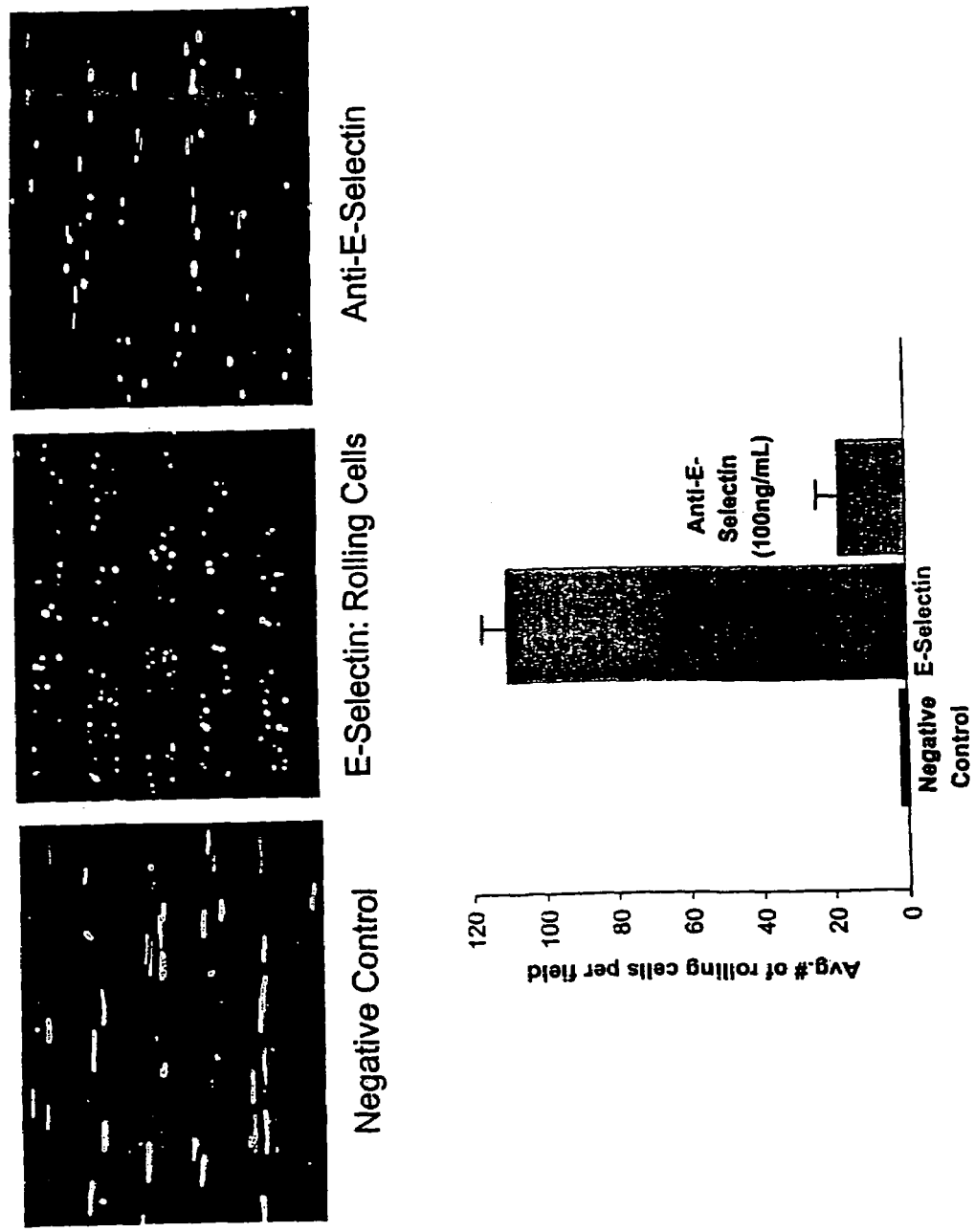
FIG. 10 is a graph and time-lapsed still photographs of cells rolling and adhering under different dilutions of E-selectin antibody.
Figure 11:
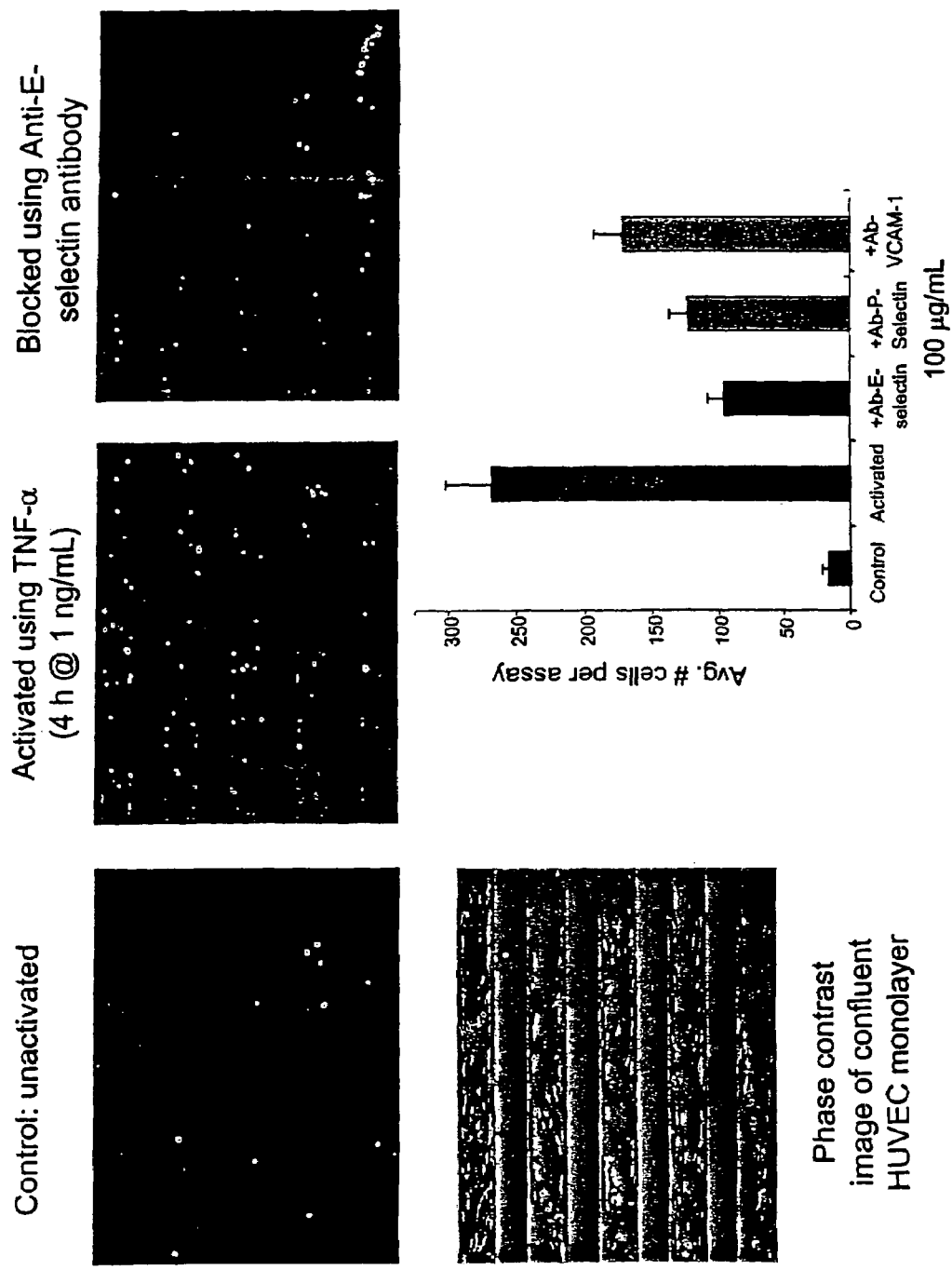
FIG. 11 is a graph and time-lapsed still photographs of cells adhering to endothelium in the presence of antibodies to E-selectin, P-selectin, and VCAM-1.

Endothelial cells are placed and activated in four different channels of four chambers (#1-#4) according to the method disclosed in section IV, part B. With respect to a fifth (#5) chamber, endothelial cells are placed in the channel, but are not activated. With respect to these five different chambers, 100 μg/ml of P-selectin antibody is pipetted into the first well of chamber #1; 100 μg/ml of E-selectin antibody is pipetted into the first well of chamber #2; 100 μg/ml of VCAM-1 antibody is pipetted into the first well of chamber #3; and 100 μg/ml of BSA in PBS is pipetted into the first well of chamber #4. The device is incubated for thirty minutes at room temperature in a dish with a cover in order to keep the wells from drying out. After incubation, the channels are washed four times with 0.1% BSA in PBS. Neutrophils in 20 μl of media are added to the first well of each chamber (about $10^3$ to about $10^6$ cells per well of a 24 well plate, in volume of 20 μl of media per well) (non-labeled and fluorescently labeled monocytic cell lines-U937 and THP-1 as well as primary leukocytes may be used). Digital images are taken on a Zeiss inverted microscope using AXIOCAM™ beginning 15 seconds after the sample comprising leukocytes is added to the first wells. Data is analyzed on AXIOVISION™ software. Time-lapsed images are taken every 30 seconds for 5 minutes and 15 seconds. 10× objective lens is used to view and record the number of cells rolling after the treatment with the antibodies as seen in FIG. 10.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

Example VII

Figure 12:
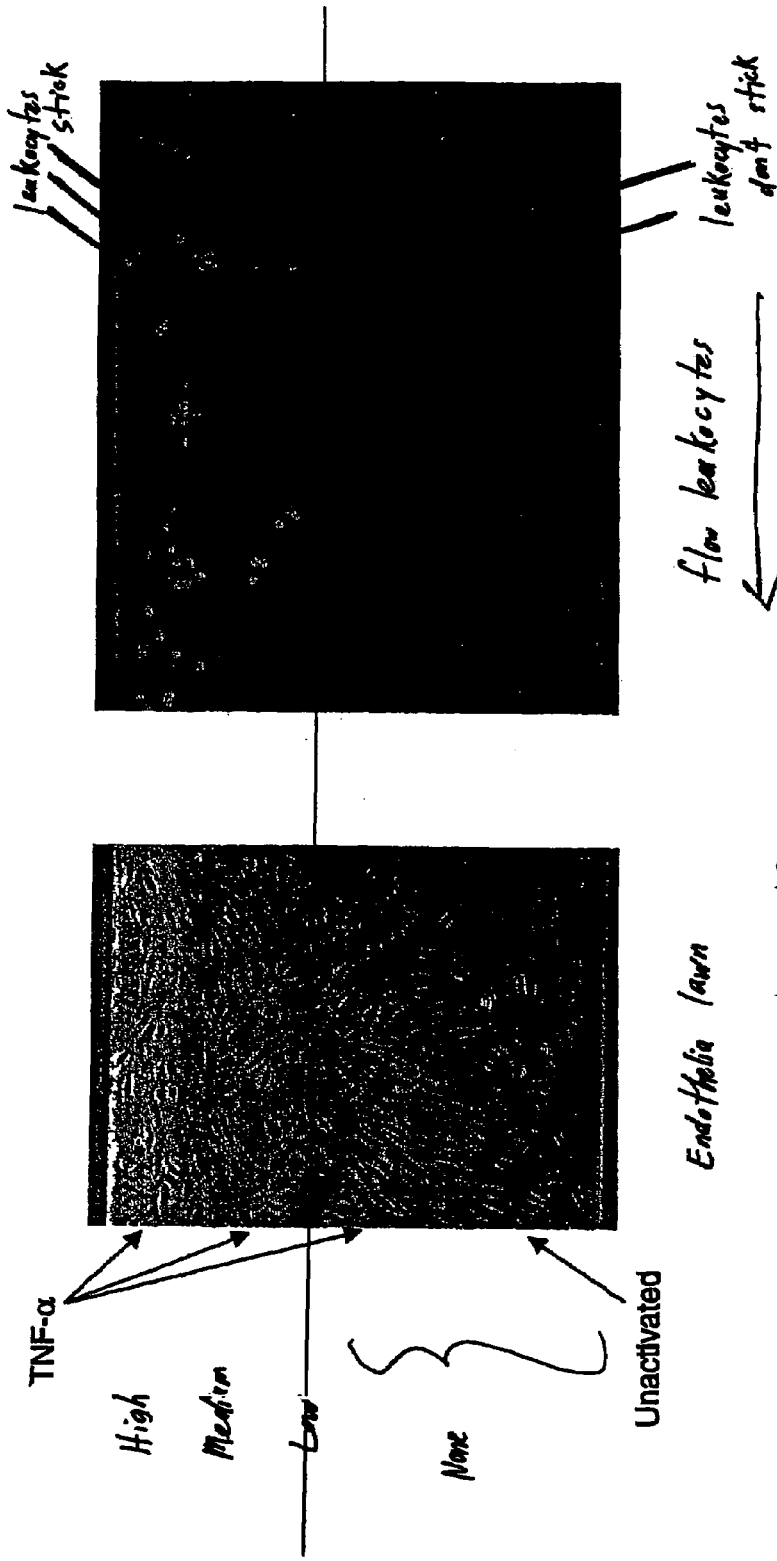
FIG. 12 depicts the results of an experiment involving the creation of a concentration gradient of TNF-α via laminar flow. The TNF-α was delivered to a confluent "lawn" of endothelial cells. The endothelial cells that were contacted by the TNF-α were activated and thus are able to bind the leukocytes. Leukocytes were then delivered to the endothelial cells. As is demonstrated in the figure, the leukocytes bound to the area of the endothelial cells that received high concentrations of TNF-α whereas those areas not exposed to TNF-α or exposed to very little TNF-α did not bind leukocytes.

Selective Activation of Endothelial Cells by Delivery of TNF-α in a Gradient Created by Laminar Flow The surface of a device of the present invention was coated with endothelial cells and allowed to grow to confluence (to create a "lawn" of cells). TNF-α was delivered to the lawn of endothelial cells via laminar flow to "activate" the endothelial cells. Each stream of solutions containing TNF-α were at different concentrations, thus creating a gradient perpendicular to the channel. This gradient effectively delivered TNF-α to the lawn of endothelial cells at different concentrations at different positions on the lawn of cells. Leukocytes were then flowed over the lawn of activated endothelial cells. Referring to FIG. 12, only those endothelial cells that were activated by TNF-α provide suitable "attachment" sites for the leukocytes. The leukocytes did not attach equally to the entire lawn, but attached to the areas of the endothelial cell lawn that had been exposed to high concentrations of TNF-α and did not attach to those areas of the lawn that had been exposed to low concentrations of TNF-α, or those areas not exposed to TNF-α at all. These results indicate that there was indeed a creation of a concentration gradient of TNF-α by the laminar flow.

We claim:

1. A system for monitoring leukocyte migration comprising:
    a device including a housing having a base member and a top member defining a plurality of chambers therein, each of the plurality of chambers including:
        a first well region including at least one first well;
        a second well region including at least one second well; and
        a channel region including at least one channel connecting the first well region and the second well region with one another,
        wherein the at least one channel is formed as a through-hole in the top member;
        a first fluid stream having a first concentration of a first substance; and
        a second fluid stream having a second concentration of a second substance,
    wherein the first and second concentrations are different from one another and the first and second fluid streams are in fluid communication with at least one of the plurality of chambers, and
    wherein the first fluid stream and the second fluid stream flow adjacent and parallel to each other without mixing, to create a dynamic concentration gradient.

2. The system of claim 1, wherein the first and second substance are the same.

3. The system of claim 1, wherein the first and second substance are different.

4. The system of claim 1, wherein the first fluid stream and the second fluid stream converge into a single third fluid stream that is in fluid communication with the at least one of the plurality of chambers, wherein the third fluid stream comprises a concentration gradient of the first and second substances, the concentration gradient being substantially perpendicular to the direction of flow of the third fluid stream.

5. The system of claim 1, wherein the first and second fluid streams converge into a single third stream, then diverge into three separate fourth, fifth, and sixth streams, and then re-converge into a single seventh stream, the seventh stream in fluid communication with the at least one of the plurality of chambers under conditions of substantially laminar flow.

6. The system of claim 1, wherein at least one of the first and second substance is a cytokine.

7. The system of claim 6, wherein the cytokine is tumor necrosis TNF-α.

8. The system of claim 1, wherein at least one of the first and second substance is a test agent.

9. A method of monitoring leukocyte migration comprising:
providing a device including a housing having a base member and a top member defining a plurality of chambers therein, each of the plurality of chambers including:
a first well region including at least one first well;
a second well region including at least one second well; and
a channel region including at least one channel connecting the first well region and the second well region with one another, wherein the at least one channel is formed as a through-hole in the top member;
disposing at least one leukocyte migration mediator, or endothelial cells in the at least one channel;
delivering a sample comprising leukocytes to the at least one channel by laminar flow; and
observing the interaction between the leukocytes and the at least one leukocyte migration mediator or the interaction between the leukocytes and the endothelial cells.

10. The method of claim 9, further comprising providing a video camera operatively linked to the device for viewing the at least one channel.

11. The method of claim 10, wherein the video camera is adapted to capture an image during predetermined intervals over a predetermined period of time.

* * * * *